(12) United States Patent
Beckman et al.

(10) Patent No.: US 7,922,656 B2
(45) Date of Patent: Apr. 12, 2011

(54) HAND ASSISTED LAPAROSCOPIC SEAL ASSEMBLY WITH DETACHABLE ATTACHMENT RING

(75) Inventors: Andrew T. Beckman, Cincinnati, OH (US); William J. White, West Chester, OH (US); Anthony Nguyen, Cincinnati, OH (US); Gregory W. Johnson, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 614 days.

(21) Appl. No.: 11/730,922

(22) Filed: Apr. 4, 2007

(65) Prior Publication Data

US 2008/0249371 A1 Oct. 9, 2008

(51) Int. Cl.
*A61B 1/32* (2006.01)
(52) U.S. Cl. ........................................ 600/204; 600/208
(58) Field of Classification Search .................. 600/204, 600/206, 208
See application file for complete search history.

(56) References Cited

U.S. PATENT DOCUMENTS

| 4,241,840 | A | 12/1980 | Willis |
| 5,514,133 | A | 5/1996 | Golub et al. |
| 5,545,179 | A | 8/1996 | Williamson, IV |
| 5,951,588 | A * | 9/1999 | Moenning ............... 606/213 |
| 6,033,426 | A | 3/2000 | Kaji |
| 6,162,172 | A * | 12/2000 | Cosgrove et al. ......... 600/208 |
| 6,254,534 | B1 * | 7/2001 | Butler et al. ............. 600/208 |
| 6,578,577 | B2 * | 6/2003 | Bonadio et al. .......... 128/850 |
| 6,908,430 | B2 | 6/2005 | Caldwell et al. |
| 6,939,296 | B2 | 9/2005 | Ewers et al. |
| 6,945,932 | B1 | 9/2005 | Caldwell et al. |
| 7,052,454 | B2 * | 5/2006 | Taylor ..................... 600/114 |
| 7,393,322 | B2 * | 7/2008 | Wenchell ................. 600/208 |
| 2004/0173218 | A1 | 9/2004 | Yamada et al. |
| 2004/0249248 | A1 * | 12/2004 | Bonadio et al. ........... 600/184 |
| 2005/0020884 | A1 * | 1/2005 | Hart et al. ................ 600/206 |
| 2005/0155611 | A1 * | 7/2005 | Vaugh et al. ............. 128/887 |
| 2005/0192483 | A1 * | 9/2005 | Bonadio et al. ........... 600/208 |
| 2005/0222582 | A1 | 10/2005 | Wenchell |
| 2005/0241647 | A1 | 11/2005 | Nguyen et al. |
| 2006/0041232 | A1 | 2/2006 | Stearns et al. |

FOREIGN PATENT DOCUMENTS

| EP | 1415610 | 7/2000 |
| EP | 1407715 | 4/2004 |
| WO | WO95/07056 | 3/1995 |
| WO | WO99/25268 | 5/1999 |
| WO | WO02/34108 | 5/2002 |
| WO | WO03/086202 | 10/2003 |
| WO | WO2004/030547 | 4/2004 |
| WO | WO2004/054456 | 7/2004 |
| WO | WO2004/075730 | 9/2004 |
| WO | WO2004/075741 | 9/2004 |
| WO | WO2004/096012 | 11/2004 |
| WO | WO2005/034766 | 4/2005 |
| WO | WO2005/097019 | 10/2005 |
| WO | WO2005/097234 | 10/2005 |

* cited by examiner

*Primary Examiner* — Eduardo C Robert
*Assistant Examiner* — Ellen C Hammond
(74) *Attorney, Agent, or Firm* — Welsh Flaxman & Gitler LLC

(57) ABSTRACT

A seal assembly for permitting hand assisted laparoscopic procedures includes a seal cap having a central access opening allowing access to a body cavity as desired. The seal cap is provided with a housing in which a seal is positioned. The seal cap also includes an attachment ring that is selectively detachable therefrom for selective attachment of a retractor.

4 Claims, 23 Drawing Sheets

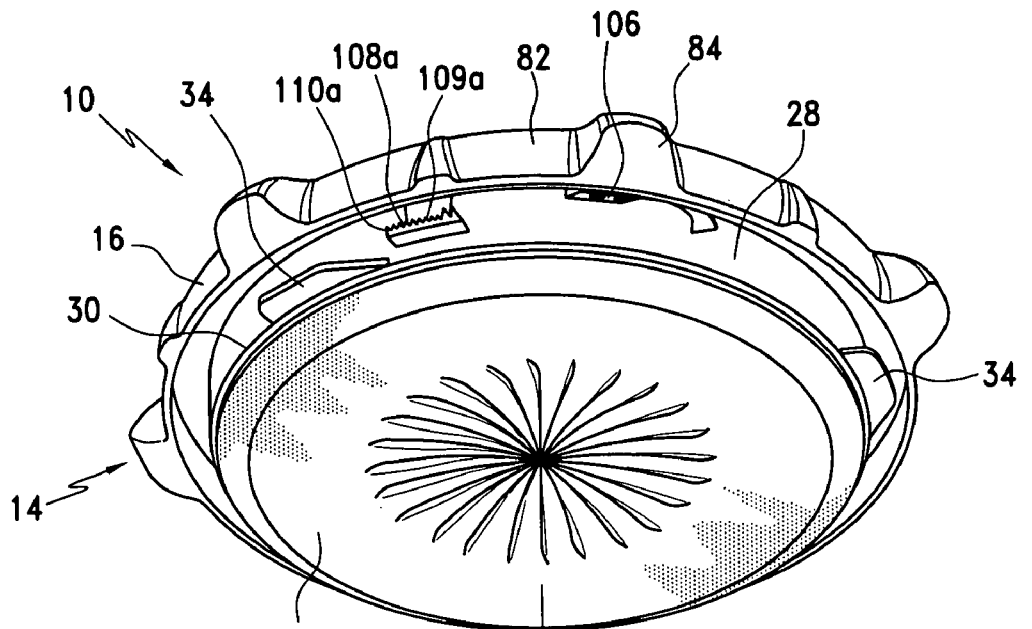
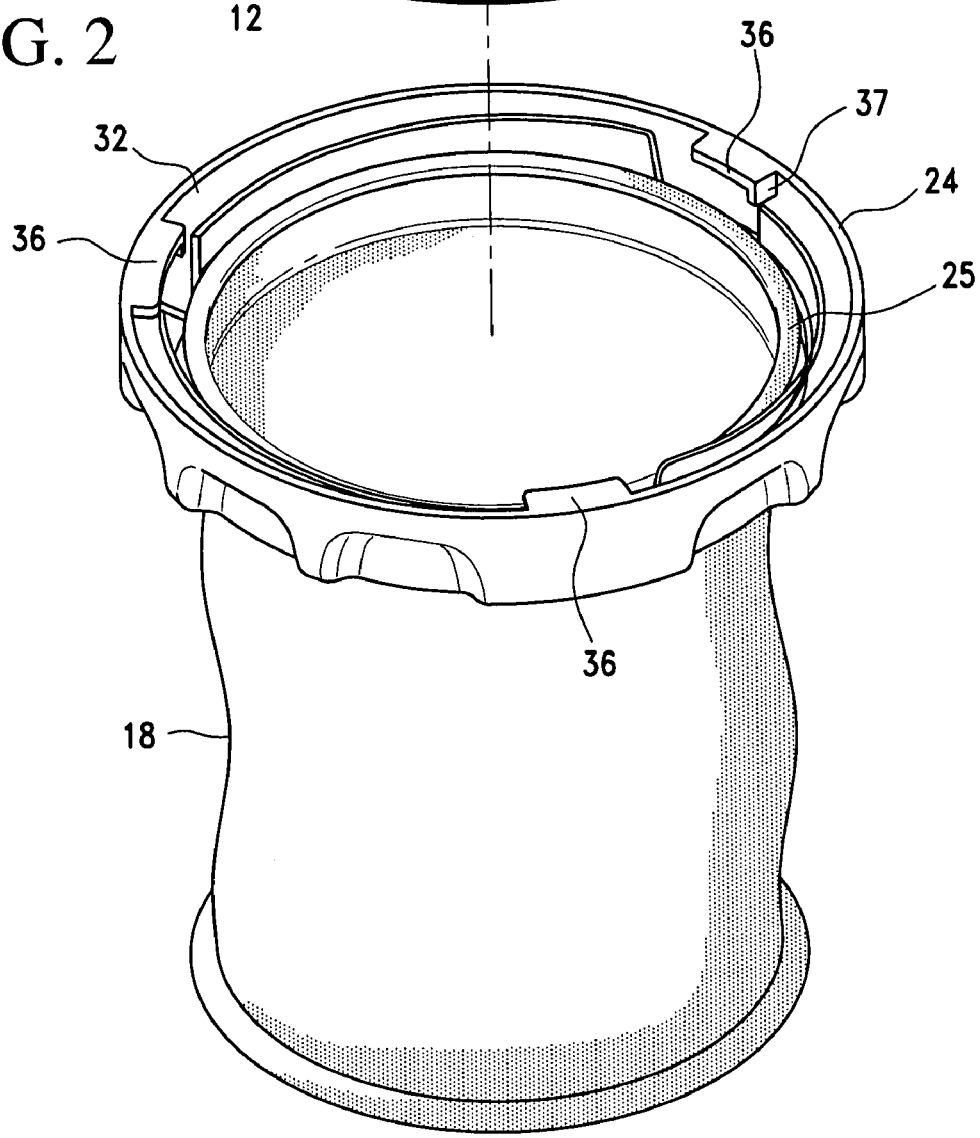
FIG. 2

FIG. 6
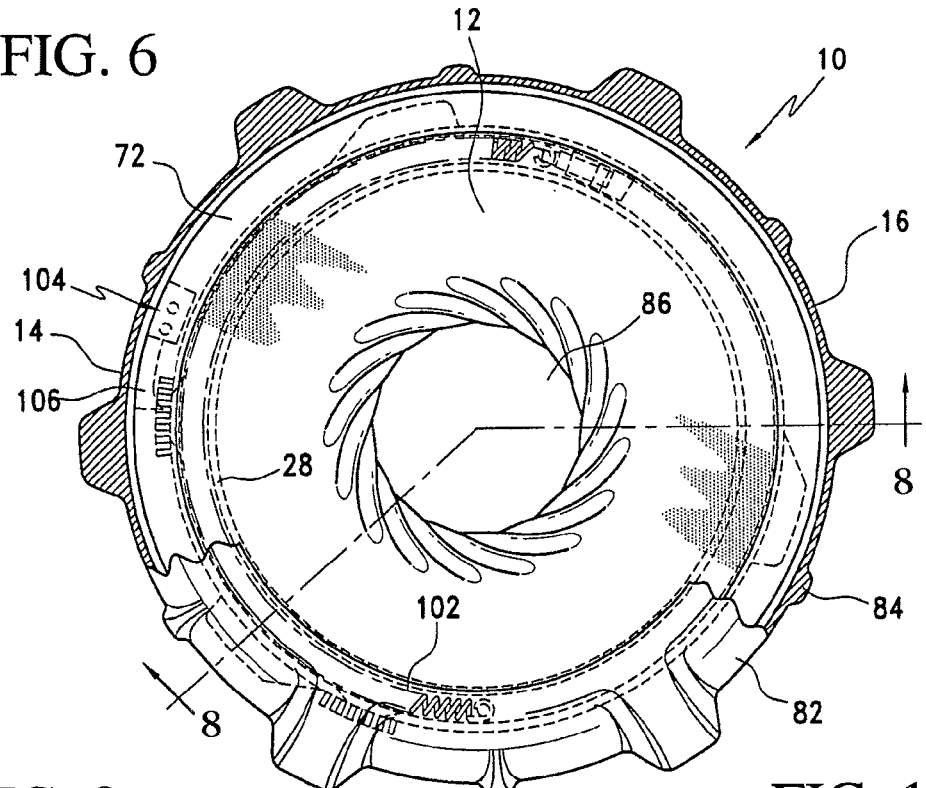
FIG. 9
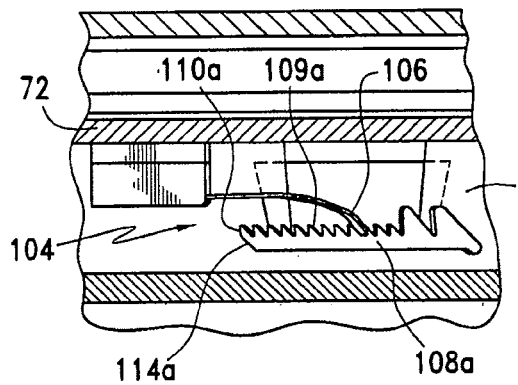
FIG. 10
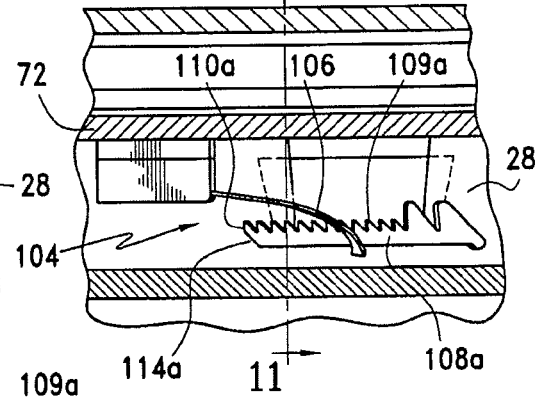
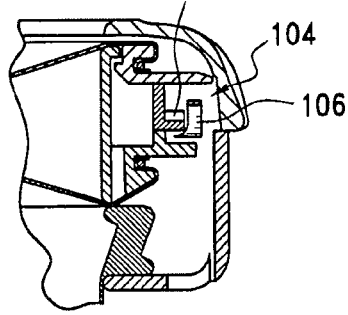
FIG. 11

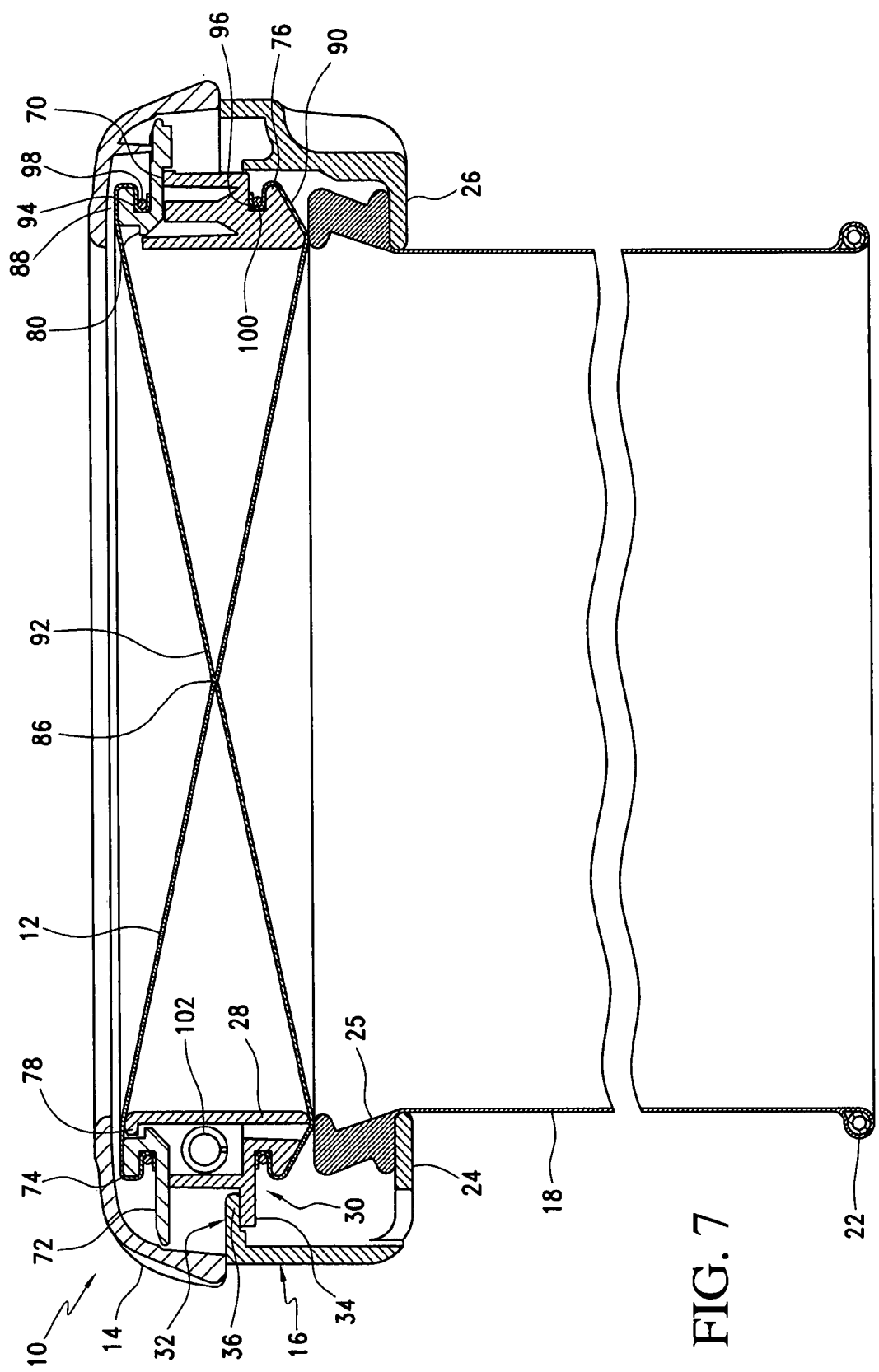

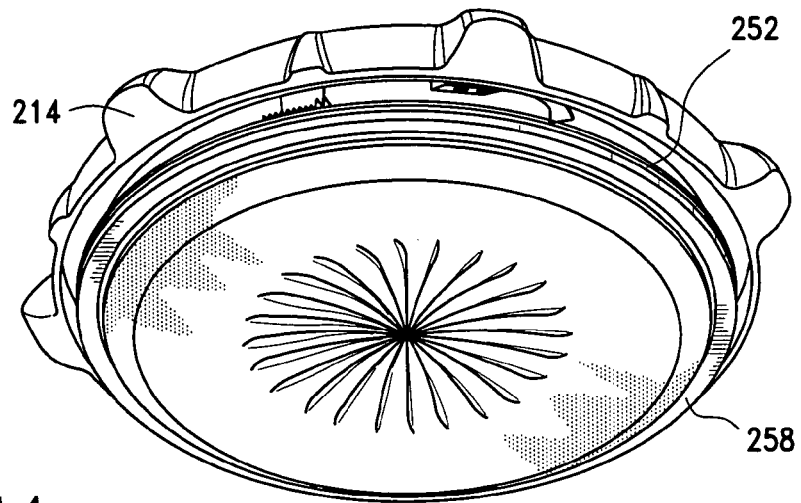
FIG. 14
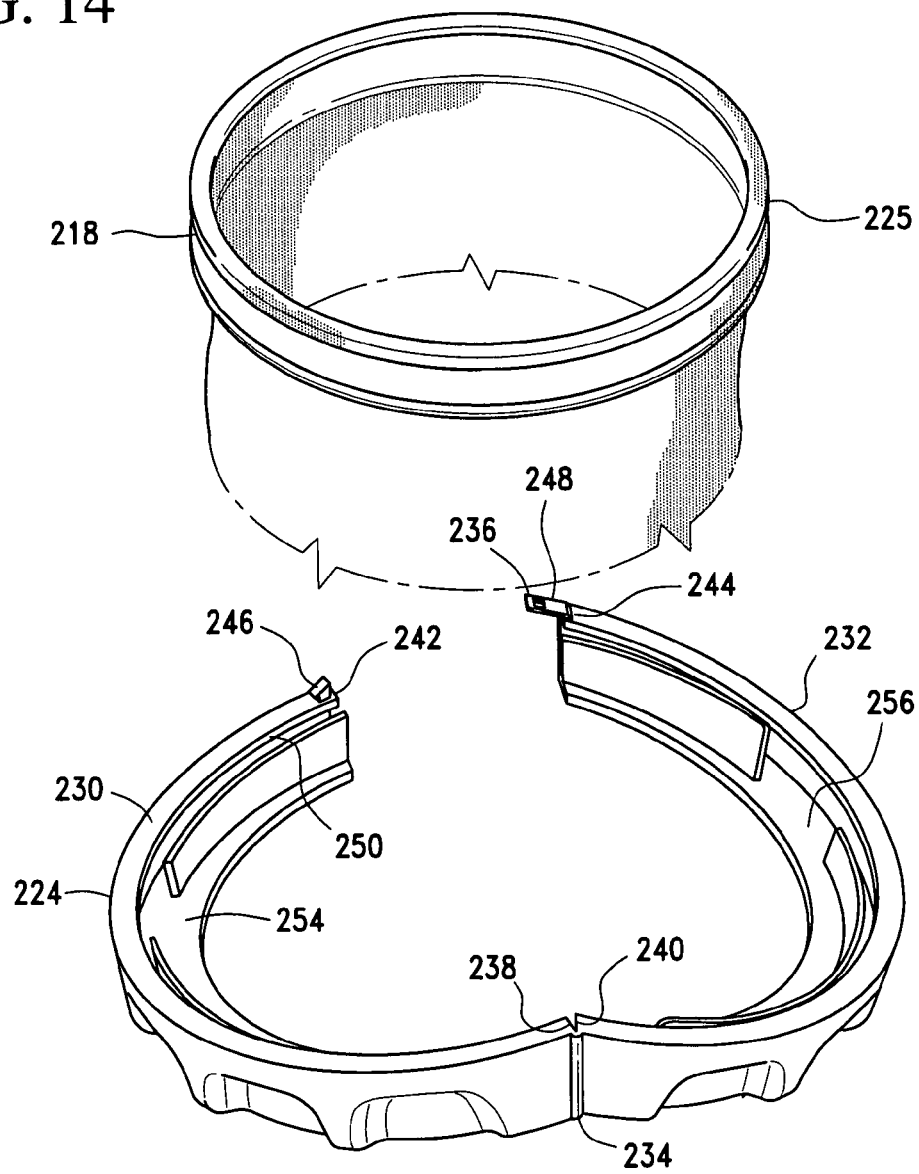

HAND ASSISTED LAPAROSCOPIC SEAL ASSEMBLY WITH DETACHABLE ATTACHMENT RING

BACKGROUND OF THE INVENTION

1. Field of the Invention

The invention relates to laparoscopic devices. In particular, the invention relates to a laparoscopic seal assembly having a detachable attachment ring for selectively securing a retractor to the seal assembly.

2. Description of the Related Art

During laparoscopic procedures, it is often desirable for the surgeon to place his or her hand within the patient in a manner manipulating the instruments positioned within the patient. When this occurs, it is desirable to separate the external environment from the internal portion of the patient. For example, when hand assisted laparoscopic procedures are performed within the abdominal cavity, it is desirable to perform hand exchanges with minimal loss of abdominal pressure.

As such, a need exists for skin mountable seals permitting hand assisted laparoscopic procedures without fear the abdominal pressure will be compromised. The present invention provides such an apparatus.

SUMMARY OF THE INVENTION

It is, therefore, an object of the present invention to provide a seal assembly for permitting hand assisted laparoscopic procedures. The seal assembly includes a seal cap having a central access opening allowing access to a body cavity as desired. The seal cap is provided with a housing in which a seal is positioned. The seal cap also includes an attachment ring that is selectively detachable therefrom for selective attachment of a retractor.

It is also an object of the present invention to provide a seal assembly wherein the seal cap includes an iris seal positioned within the housing.

It is also another object of the present invention to provide a seal assembly wherein the attachment ring includes a ledge upon which an upper end of a retractor is seated to securely position it between the attachment ring and a lower member of the housing.

It is also a further object of the present invention to provide a seal assembly wherein the seal cap includes an upper seal ring and a lower seal ring, and the attachment ring is selectively secured to the lower seal ring.

It is still a further object of the present invention to provide a seal assembly wherein the lower seal ring is formed with a plurality of outwardly extending flanges shaped and dimensioned for seating within inwardly facing recesses formed along the attachment ring such that one need only place the lower seal ring within a space defined by the attachment ring and subsequently twist the outwardly extending flanges into the inwardly extending recesses to securely couple the attachment ring to the lower seal ring.

It is yet a further object of the present invention to provide a seal assembly wherein the inwardly extending recesses of the attachment ring are provided with a transverse wall that stops rotation of the lower seal ring relative to the attachment ring.

It is another object of the present invention to provide a seal assembly wherein the attachment ring is constructed with a first semi-circular member and a second semi-circular member.

It is still another object of the present invention to provide a seal assembly wherein each of the first semi-circular member and the second semi-circular member includes a first end and second end, and the respective first ends of the first semi-circular member and the second semi-circular member are connected via a living hinge in a manner allowing the first semi-circular member and the second semi-circular member to pivot relative to each other, and the second ends of the first semi-circular member and the second semi-circular member are respectively provided with a first latch member and a second mating latch member shaped and dimensioned to provide for selective coupling and decoupling of the second ends of the first semi-circular member and the second semi-circular member.

It is also a further object of the present invention to provide a seal assembly wherein the attachment ring includes an inwardly directed, upper connecting flange shaped and dimensioned to seat within a recess formed along an outer circumference of the seal cap and a lower connecting flange shaped and dimensioned for receiving and supporting an upper end of a retractor.

It is another object of the present invention to provide a seal assembly wherein the attachment ring includes an inwardly directed first upper connecting flange and an inwardly directed second upper connecting flange.

It is also an object of the present invention to provide a seal assembly wherein the attachment ring is further provided with an inwardly directed, lower connecting flange shaped and dimensioned for receiving and supporting an upper end of a retractor.

It is a further object of the present invention to provide a seal assembly wherein the first upper connecting flange is shaped and dimensioned to extend to engage an outwardly extending lip of the seal cap.

It is still another object of the present invention to provide a seal assembly wherein the first upper connecting flange is generally arcuate in shape as it extends about a small portion of a circumference of the attachment ring and the second upper connecting flange includes an inwardly directed protrusion shaped and dimensioned to seat within a recess formed along an outer body of the seal cap, wherein interaction of the first upper connecting flange and the second upper connecting flange results in a secure attachment of the attachment ring.

It is also an object of the present invention to provide a seal assembly wherein the attachment ring includes an inwardly directed, first upper connecting flange which is biased under control of a spring for selective attachment and release of the attachment ring.

It is a further object of the present invention to provide a seal assembly wherein the attachment ring is further provided with an inwardly directed, lower connecting flange shaped and dimensioned for receiving and supporting an upper end of the retractor.

It is another object of the present invention to provide a seal assembly wherein the attachment ring is further provided with an inwardly directed, second upper connecting flange and the second upper connecting flange is fixed and is substantially, diametrically opposed to the first upper connecting flange.

It is also another object of the present invention to provide a seal assembly wherein the attachment ring includes a safety cap type attachment mechanism for selective attachment to the seal cap.

It is yet another object of the present invention to provide a seal assembly including a retractor selectively secured to the seal cap.

It is still another object of the present invention to provide a seal assembly wherein the attachment ring includes at least one latch shaped and dimensioned to selectively engage the remainder of the seal cap.

It is also an object of the present invention to provide a seal assembly wherein the at least one latch is resiliently biased.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 2 is a perspective view of the hand assisted laparoscopic seal assembly with the attachment ring and retractor disengaged from the seal cap.

FIGS. 4, 5 and 6 are partial sectional top views showing actuation of the present hand assisted laparoscopic seal assembly respectively between a closed position, a partially opened orientation for hand insertion and a fully opened orientation for viewing and insertion of larger instruments.

FIG. 7 is a cross sectional view taken along the line 7-7 in FIG. 4.

FIGS. 9, 10 and 11 are detailed views of the ratchet mechanism in accordance with the present invention.

FIG. 14 is an exploded view of the hand assisted laparoscopic seal assembly shown with reference to FIG. 13.

DESCRIPTION OF THE PREFERRED EMBODIMENTS

Figure 1:
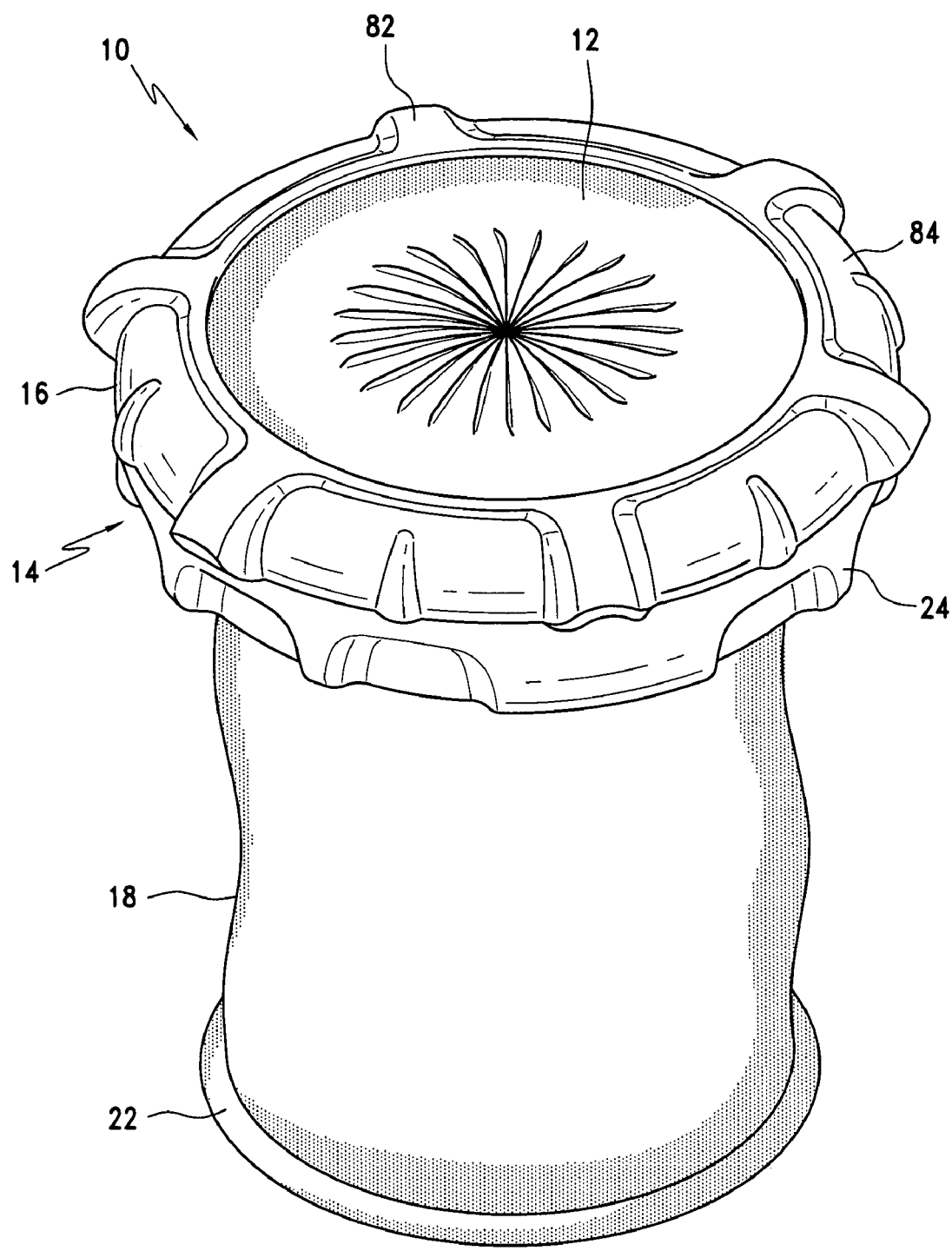
FIG. 1 is a perspective view of the present hand assisted laparoscopic seal assembly.
Figure 3:
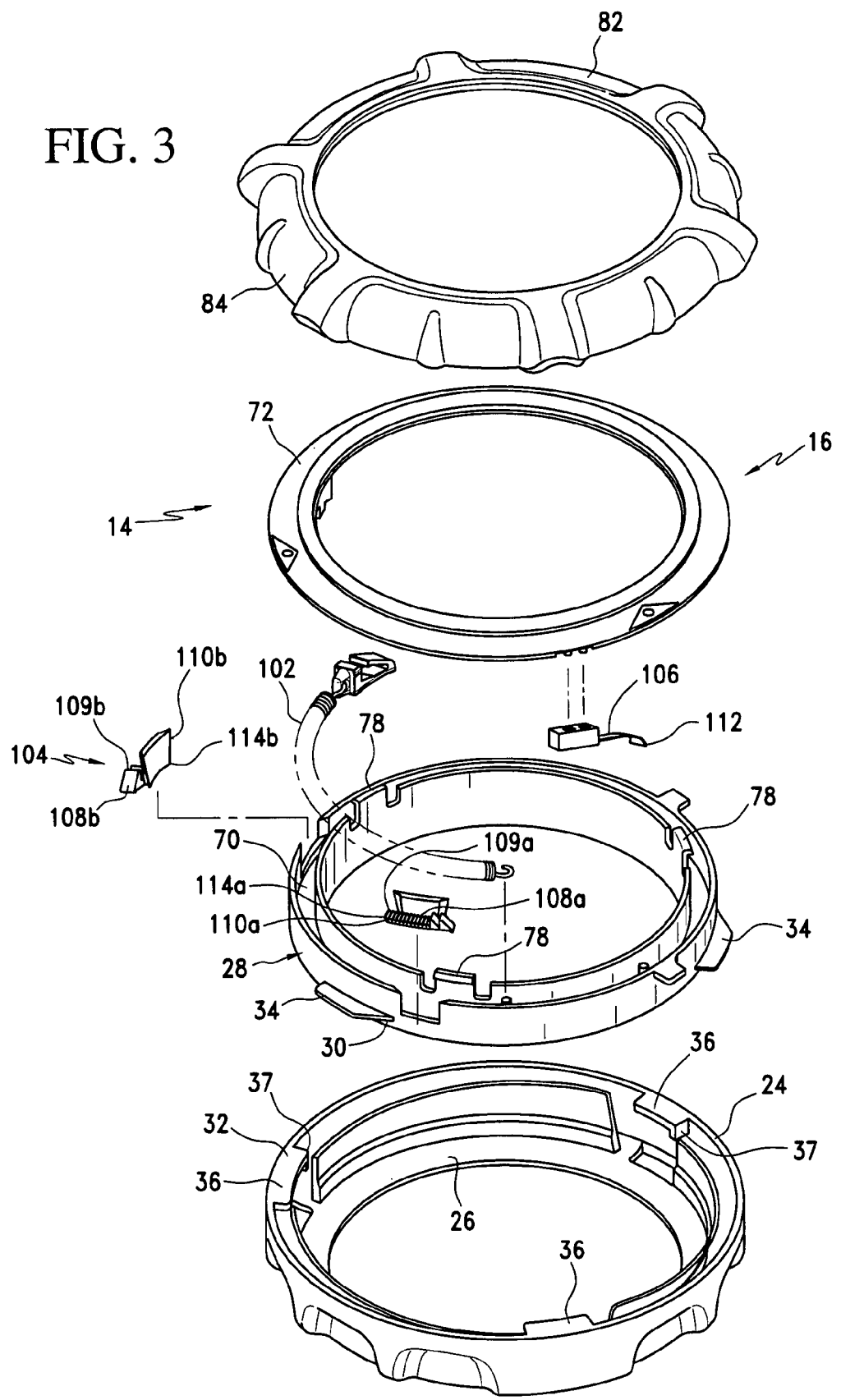
FIG. 3 is an exploded view of the seal cap of the present seal assembly.
Figure 4:
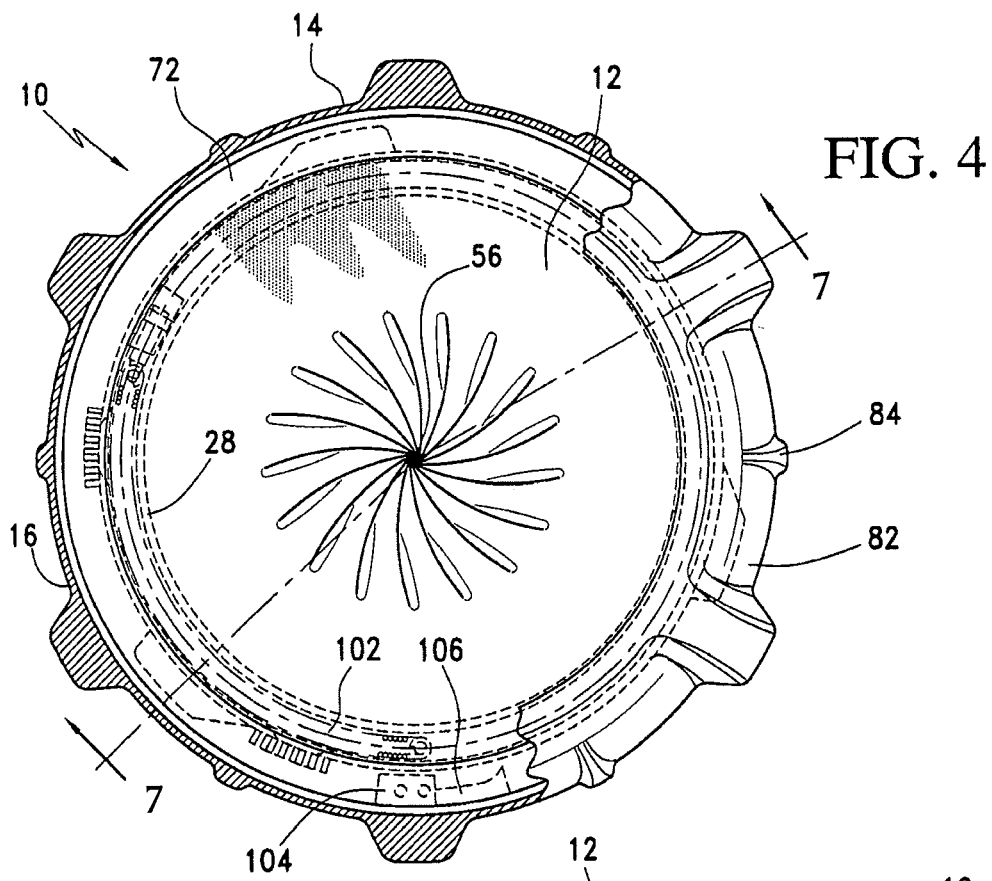

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for teaching one skilled in the art how to make and/or use the invention.

Referring to FIGS. 1 to 11, a seal assembly 10 for permitting hand assisted laparoscopic procedures is disclosed. The seal assembly 10 generally employs an iris seal cap 14 and retractor 18 to ensure abdominal pressure is not compromised during hand exchanges while hand assisted laparoscopic procedures are performed. As such, and in accordance with a preferred embodiment of the present invention, the seal assembly 10 includes an iris seal 12 housed within a seal cap 14. The iris seal 12 includes a central access opening 86 allowing access to the body cavity as desired by the surgeon, or other medical practitioner, performing the procedure. As a result the iris seal 12 is shaped and dimensioned to create a gas tight barrier around the surgeon's wrist when inserted through the seal assembly 10 and also creates a gas tight barrier between the interior abdominal space and the external environment when a hand is not inserted through the seal assembly 10. As will be discussed below in greater detail, adjustment of the iris seal 12, and ultimately the access opening 86, provides for access to the body cavity in this highly controlled manner.

Referring to the various figures, the seal cap 14 includes an iris seal 12 positioned within a housing 16. The housing 16 is made of soft textured material such as the thermoplastic elastomer SANTOPRENE, or other like materials, and supports the iris seal 12 in a concentric manner. Although SANTOPRENE is disclosed in accordance with a preferred embodiment, other housing materials may be used without departing from the spirit of the present invention.

As with prior hand assisted laparoscopic seal assemblies, the housing 16 of the present seal assembly 10 is secured to the abdominal wall 20 of an individual patient by first creating an incision and positioning the retractor 18 above the incision. Thereafter, the retractor 18, which will eventually be coupled to the seal cap 14, is inserted into the body cavity with the abdominal wall 20 therebetween. The seal cap 14 is then connected to the retractor 18 in a manner securely connecting and supporting the seal cap 14 on the outside of the abdominal wall 20 with the abdominal wall 20 resiliently held between the seal cap 14 and the retractor 18.

More particularly, the surgical site is prepared in accordance with conventional standard hospital procedures, making sure the skin is clean and dry. Thereafter, a template is placed over the incision site and an incision line is marked upon the template using a sterile skin marker. As those skilled in the art will appreciate, the glove size dictates the size of the incision. For example, if the surgeon's glove size is 7, a 6.5 to 7.0 cm incision is usually appropriate. Thereafter, an incision is made along the marked incision line. The incision size is thereafter verified by inserting the surgeon's hand into the abdomen prior to installing the retractor 18 and the present seal cap 14. If the incision is too small, the incision is extended on each end as required to maintain the central position of the incision relative to the placement of the present seal assembly 10. Thereafter, the back band 22 of the retractor 18 is inserted through the incision. Using one's fingers, the retractor 18 is seated evenly under the peritoneum and the area is swept to ensure the retractor 18 is not lying between tissue layers. Thereafter, the seal cap 14 is attached to the retractor 18 via an attachment ring 24, which may be rigid but is not limited to such construction, and adjustments are made to ensure the seal assembly 10 is secured with the patient's abdomen maintaining pneumo. As those skilled in the art will certainly appreciate, the retractor may be a fixed length or adjustable length retractor. In either case, the retractor 18 must fit the abdominal wall thickness to maintain stability and pneumo. As briefly discussed above, the present seal assembly 10 is provided with an attachment ring 24, which ultimately forms part of the housing 16 of the seal cap 14 when it is secured thereto in the manner discussed below in greater detail, that is detachable from the remaining portions of the housing 16 for permitting selective attachment of the retractor 18 to the present seal cap 14. It is further contemplated the attachment ring 24 can facilitate other accessory cap attachments, such as instrument port cap.

In particular, the upper end 25 of the retractor 18 is seated upon a ledge 26 formed in the attachment ring 24 (best seen in FIG. 7). Thereafter, the attachment ring 24 is secured to the remainder of the housing 16 such that the retractor 18 is securely positioned between the attachment ring 24 and a lower seal ring 28 of the seal cap 14.

Selective attachment and detachment of the attachment ring 24 from the lower seal ring 28 is achieved through the provision of interlocking engagement structures formed along the lower surface 30 of the lower seal ring 28 and the upper surface 32 of the attachment ring 24. In particular, the lower seal ring 28 is formed with a plurality of outwardly extending flanges 34 that are shaped and dimensioned for seating within inwardly facing recesses 36 formed along the attachment ring 24. As such, one need only place the lower seal ring 28 within the space defined by the attachment ring 24 and subsequently twist the outwardly extending flanges 34 into the inwardly extending recesses 36 to securely couple the attachment ring 24 to the lower seal ring 28, and ultimately to the remainder of the housing 16 of the seal cap 14. Rotation of the lower seal ring 28 relative to the attachment ring 24 is controlled by providing the recesses 36 with a transverse wall 37 that stops rotation of the lower seal ring 28 relative to the attachment ring 24. The wall 37 is positioned on the side of the recess 36 that is in the same rotational direction as the direction to open the iris seal 12 (and in accordance with a preferred embodiment, clockwise). When it is desired to detach the attachment ring 24 from the lower seal ring 28, one need only turn the lower seal ring 28 in the opposite direction, that is, counter-clockwise in accordance with a preferred embodiment, with slight pressure to overcome the frictional interference between the outwardly extending flanges 34 of the lower seal ring 28 and the inwardly directed recesses 36 of the attachment ring 24 such that the flanges 34 and recesses 36 are unseated in a manner permitting separation of the attachment ring 24 and the lower seal ring 28. It will be understood by those skilled in the art that the disconnect torque must be greater than the rotational torque of the iris seal 12.

Figure 13:
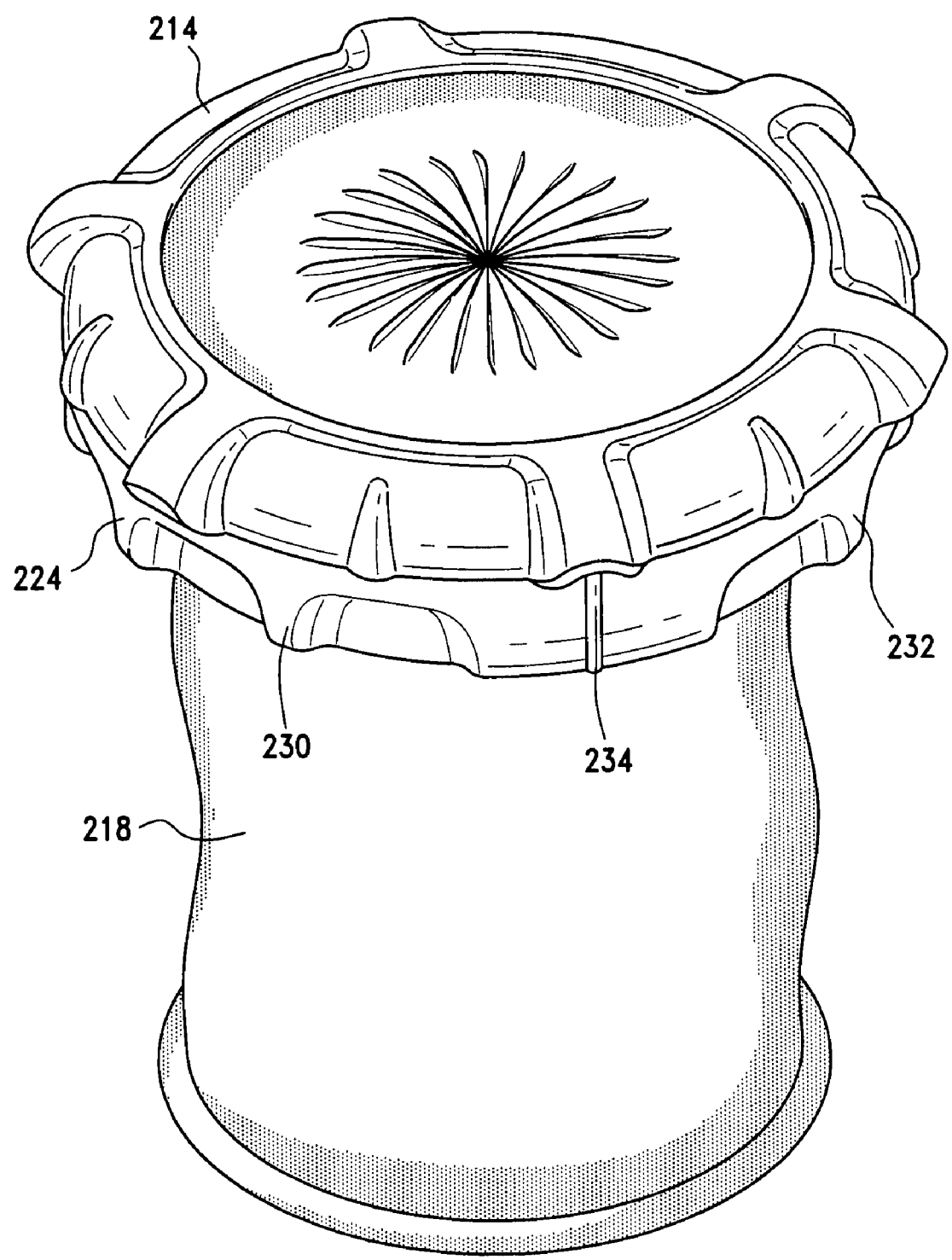
FIG. 13 is a perspective view of a hand assisted laparoscopic seal assembly with an alternate attachment ring.
Figure 15:
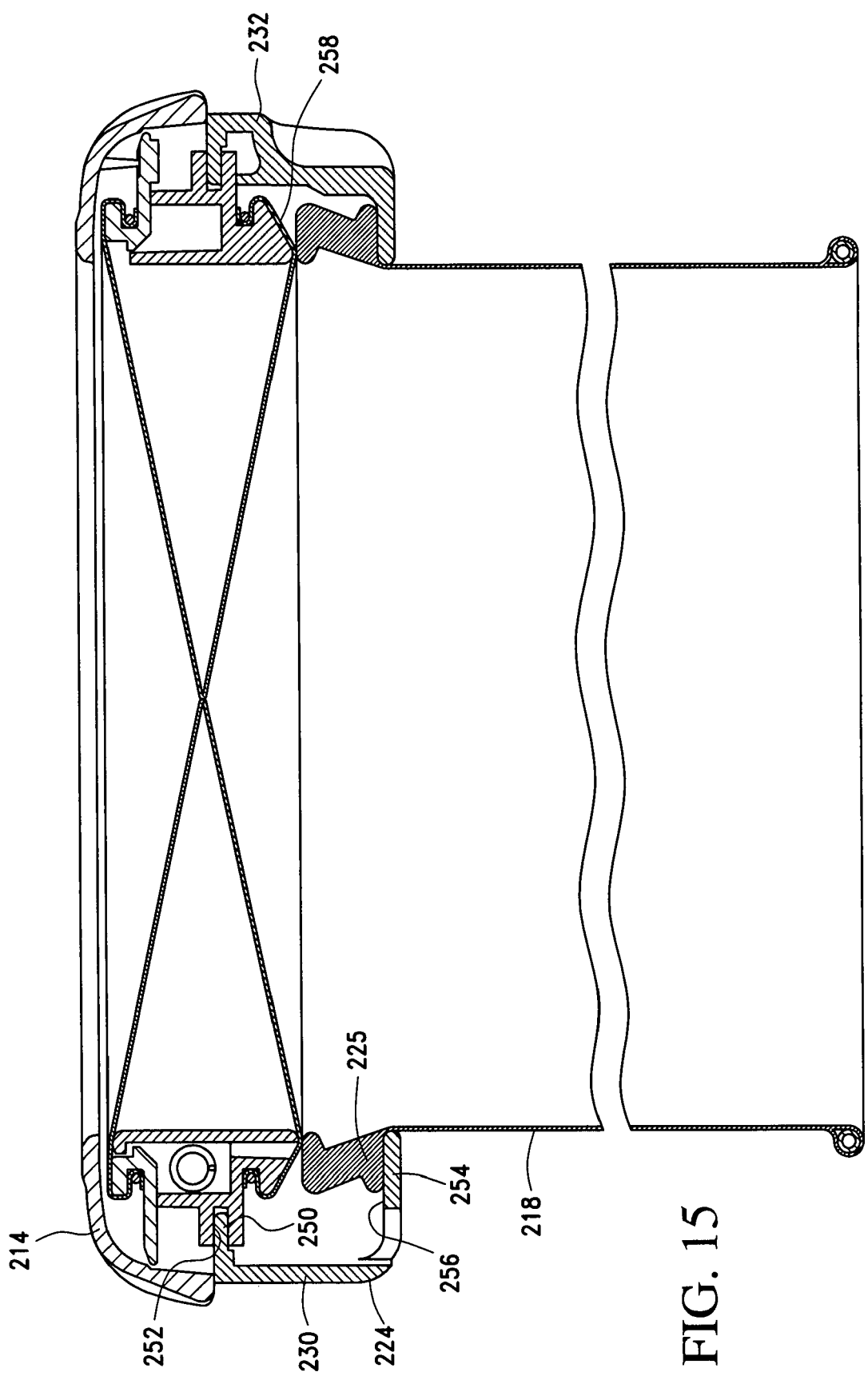
FIG. 15 is a cross sectional view of the hand assisted laparoscopic seal assembly shown with reference to FIG. 13.

In accordance with an alternate embodiment, and with references to FIGS. 13, 14 and 15, the attachment ring 224 is constructed with first and second semi-circular members 230, 232 connected via a living hinge 234 at one end and a latch 236 at the other end. More particularly, each of the first and second semi-circular members 230, 232 include a first end 238, 240 and second end 242, 244. The respective first ends 238, 240 of the first and second semi-circular members 230, 232 are connected via the living hinge 234 in a manner allowing the first and second semi-circular members 230, 232 to pivot relative to each other. In this way the respective second ends 242, 244 of the first and second semi-circular members 230, 232 may be moved between a locked position wherein the first and second semi-circular members 230, 232 define a circle (see FIGS. 13 and 15) and an open configuration where the second ends 242, 244 the first and second semi-circular members 230, 232 are spaced apart from each other in a manner allowing access to the space defined by first and second semi-circular members 230, 232 (see FIG. 14).

With the foregoing in mind, the second ends 242, 244 of the first and second semi-circular members 230, 232 are provided with first and second mating latch members 246, 248. The first and second latch members 246, 248 are shaped and dimensioned to provide for selective coupling and decoupling of the second ends 242, 244 of the first and second semi-circular members 230, 232.

Secure attachment of the attachment ring 224 to the seal cap 214 with a retractor 218 secured thereto is achieved by providing the attachment ring 224 with an inwardly directed, upper connecting flange 250 shaped and dimensioned to seat within a recess 252 formed along the outer circumference of the seal cap 214 when the attachment ring 224 is placed around the seal cap 214 and in its locked position. The attachment ring 224 is further provided with an inwardly directed, lower connecting flange 254 shaped and dimensioned for receiving and supporting the upper end 225 of the retractor 218. In particular, the lower connecting flange 254 is shaped and dimensioned such that the upper end 225 of the retractor 218 is held between the bottom of the seal cap 214 and the upper surface 256 of the lower connecting flange 254.

In practice, the upper end 225 of the retractor 218 is placed within the attachment ring 224 while the attachment ring 224 is in its open configuration. Thereafter, the attachment ring 224 is placed about the seal cap 214 with the upper connecting flange 250 positioned to engage the recess 252 of the seal cap 214 and the upper end 225 of the retractor 218 positioned for coupling between the bottom 258 of the seal cap 214 and the upper surface 256 of the lower connecting flange 254. At this point, the second ends 242, 244 of the first and second ring members 230, 232 are brought together and the first and second latch members 246, 248 are coupled together in a manner locking the attachment ring 224 to the seal cap 214. The attachment ring 224, and ultimately, the seal cap 214 may be subsequently removed by simply detaching the first and second latch members 246, 248 and removing the attachment ring 224 from the seal cap 214.

Figure 16:
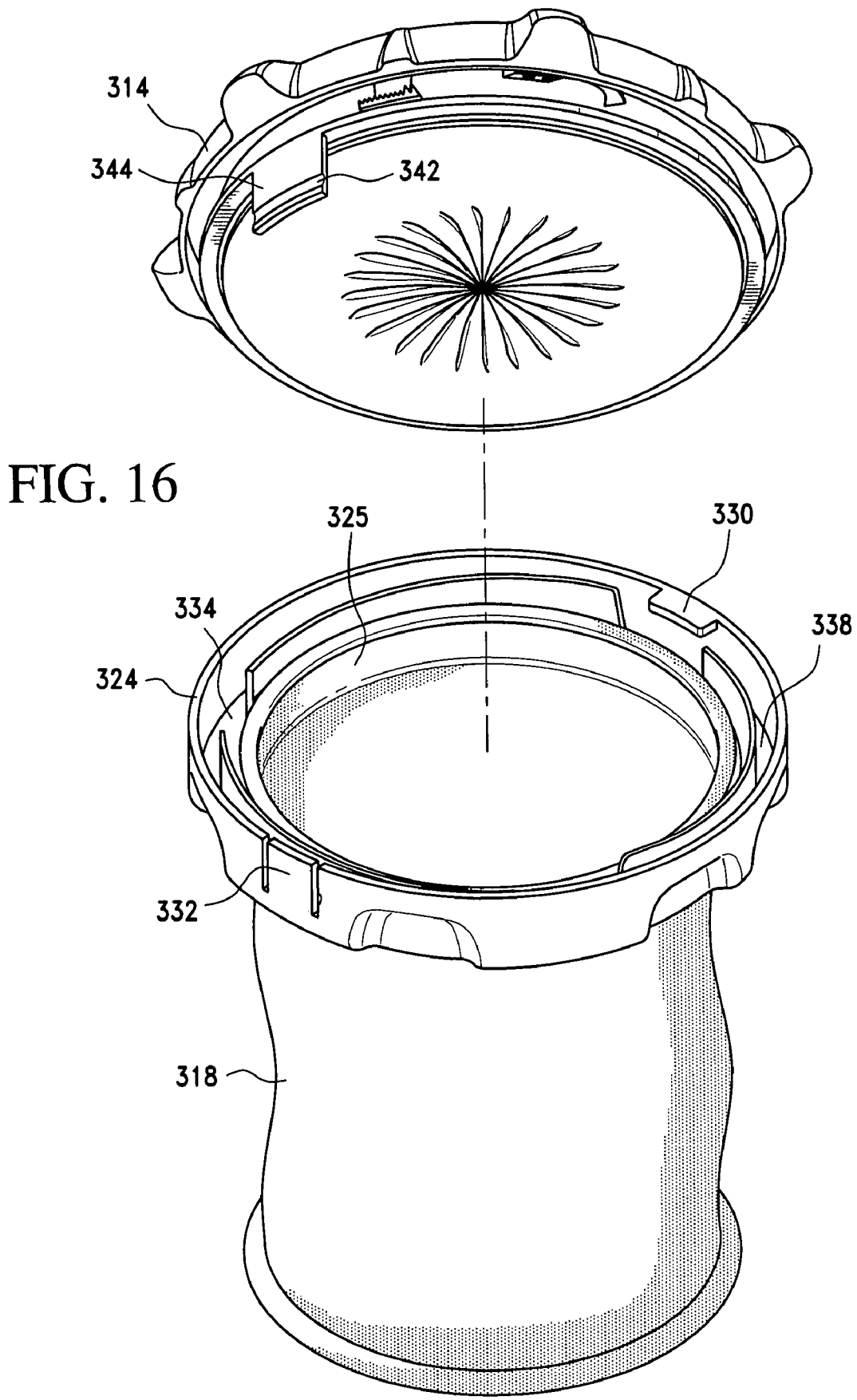
FIG. 16 is an exploded perspective view of a hand assisted laparoscopic seal assembly with a further alternate attachment ring.
Figure 17:
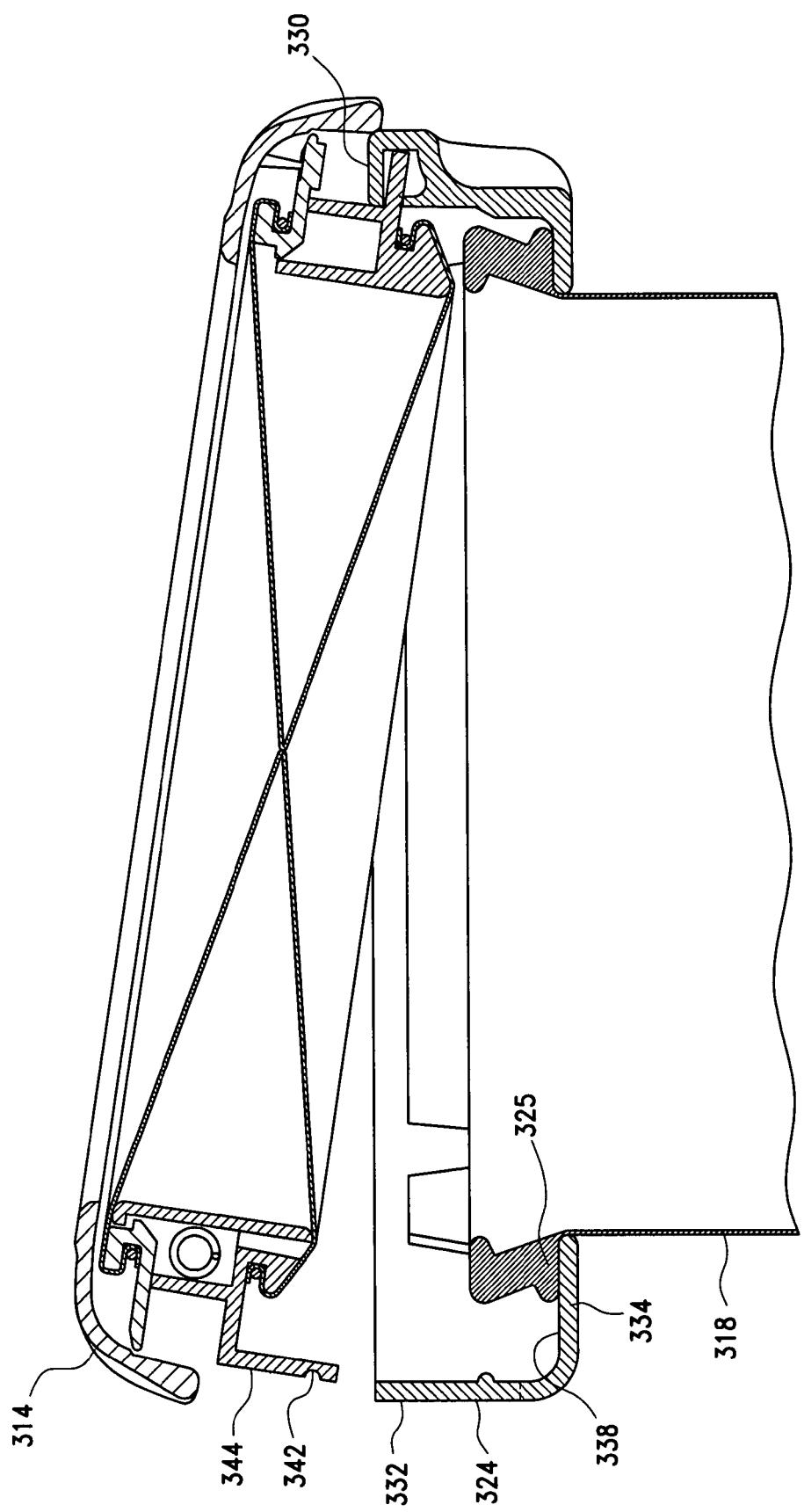
FIGS. 17 and 18 ate cross sectional views showing attachment of the hand assisted laparoscopic seal assembly shown with reference to FIG. 16.
Figure 18:
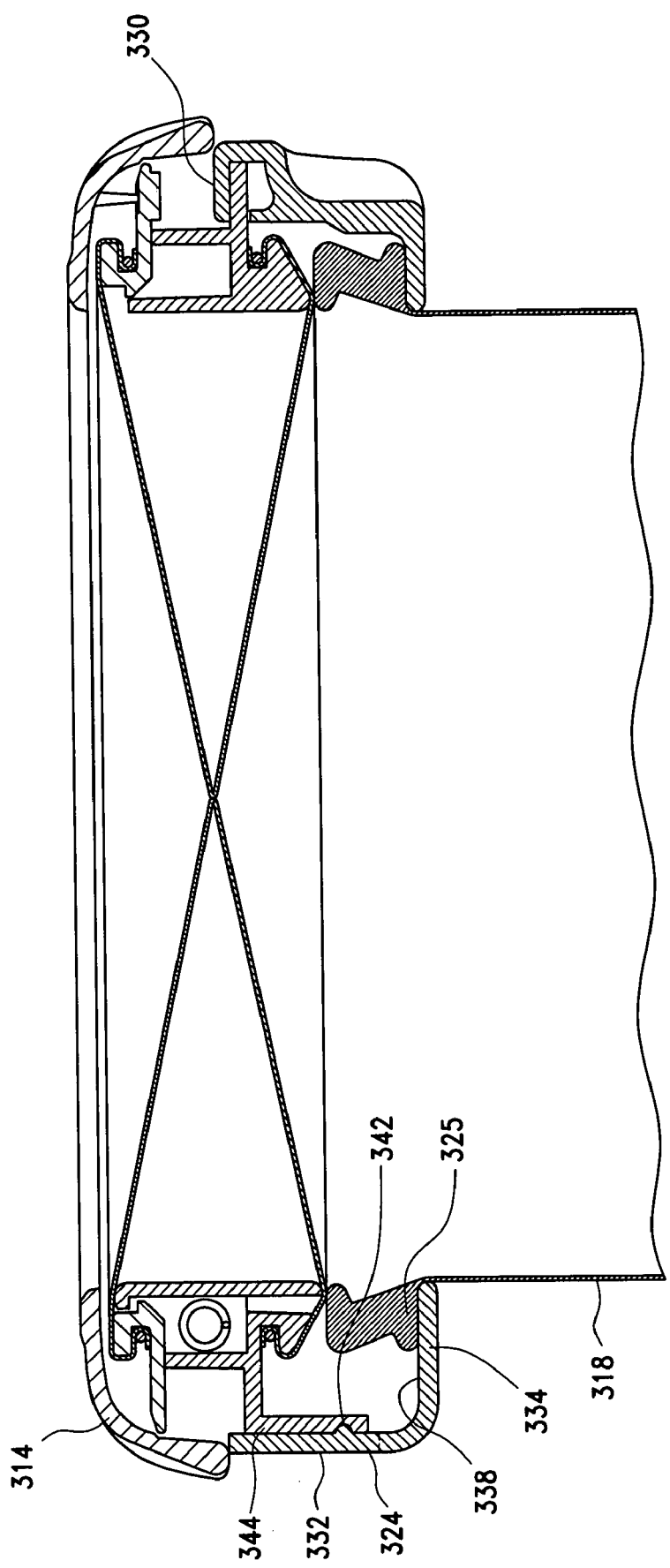

Referring to FIGS. 16, 17 and 18, yet a further embodiment of an attachment ring 324 is disclosed for use in selectively securing a retractor 318 to a seal cap 314. As with the prior embodiment, the attachment ring 324 is selectively secured to the seal cap 314 for attachment and replacement of the retractor 318. This is achieved by providing the attachment ring 324 with inwardly directed, first and second upper connecting flanges 330, 332. The attachment ring 324 is further provided with an inwardly directed, lower connecting flange 334 shaped and dimensioned for receiving and supporting the upper end 325 of the retractor 318. The lower connecting flange 334 is shaped and dimensioned such that the upper end 325 of the retractor 318 is held between the bottom of the seal cap 314 and the upper surface 338 of the lower connecting flange 334.

The first upper connecting flange 330 is shaped and dimensioned to extend to engage an outwardly extending lip 340 of the seal cap 314 such that both the seal cap 314 and the upper end 325 of the retractor 318 are securely held between the first upper connecting flange 330 and the lower connecting flange 334. The first upper connecting flange 330 is generally arcuate in shape as it extends about a small portion of the circumference of the attachment ring 324. The extent of the arc covered by the first upper connecting flange 330 is determined by desired force for removal and attachment of the attachment ring 324 and seal cap 314.

The second upper connecting flange 332 includes an inwardly directed protrusion 333 which is shaped and dimensioned to seat within a recess 342 formed along the outer body of the seal cap 314. In this way, the interaction of the first and second upper connecting flanges 330, 332 results in a secure attachment of the attachment ring 324 and the seal cap 314. In practice, the upper end 325 of the retractor 318 is placed within the attachment ring 324 and positioned upon the upper surface 338 of the lower connecting flange 334. Thereafter, the seal cap 314 is oriented at an oblique angle with respect to the attachment ring 324 such that a leading end of the seal cap 314 may be slid within the space defined thereby with the leading end of the seal cap 314 substantially positioned between the first upper connecting flange 330 and the lower connecting flange 334. At this point the seal cap 314 is rotated, in particular, the trailing end of the seal cap 314 is rotated toward the lower connecting flange 334 such that the second upper connecting flange 332 rides along the outer wall 344 of the seal cap 314 until its protrusion 333 seats within the recess 342 formed therein. At this point, the seal cap 314 should be securely held within the attachment ring 324 with the retractor 318 held between the lower connecting flange 334 and the lower surface of the seal cap 314. The attachment ring 324, and ultimately, the seal cap 314 may be subsequently removed by simply reversing the preceding steps; generally, that is, prying the second upper connecting flange 332 from within the recess 342 along the outer wall of the seal cap 314, rotating the trailing end of the seal cap 314 away from the lower connecting flange 334 and withdrawing the leading end from its position within the space defined by the attachment ring 324.

Figure 19:
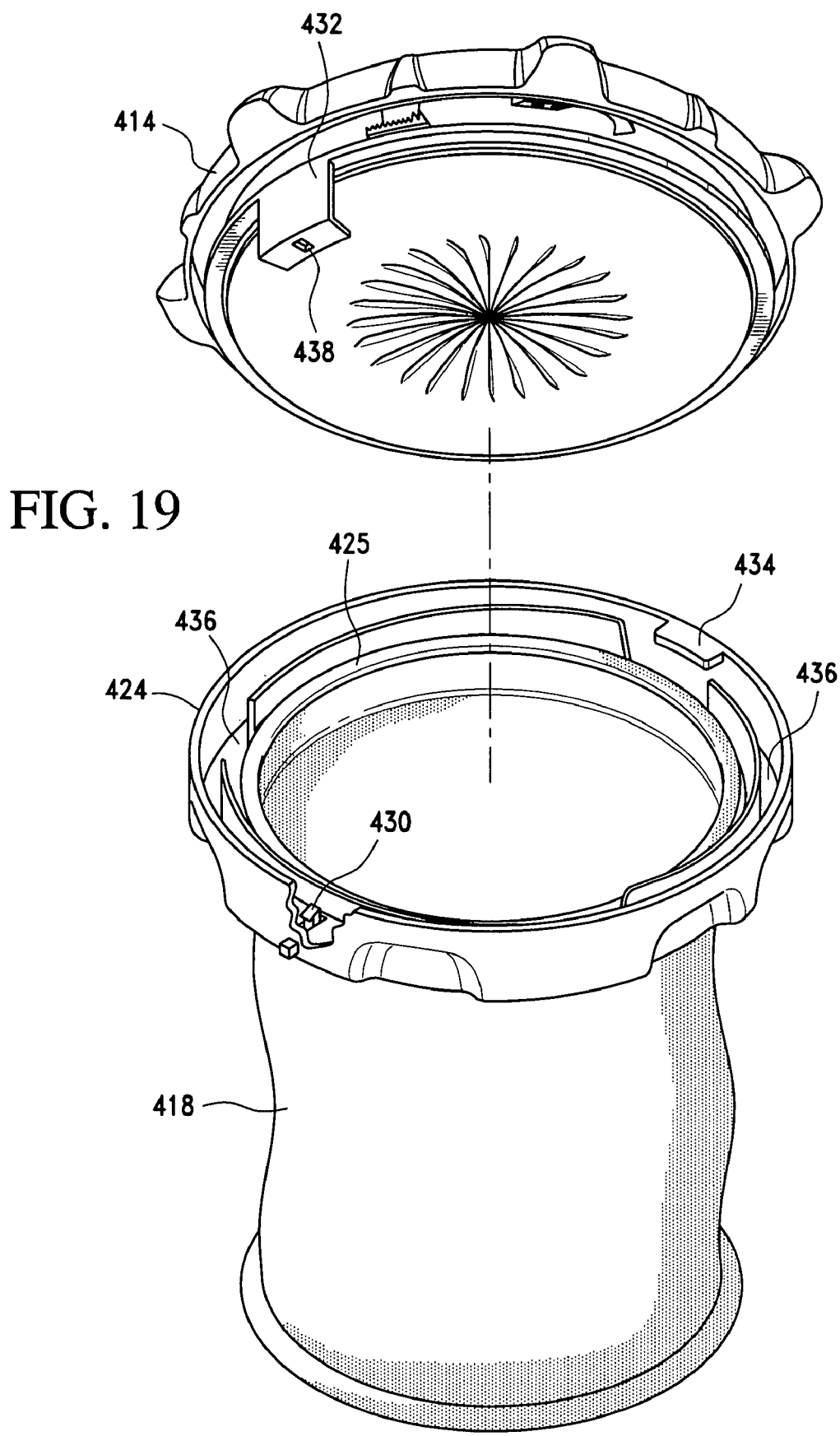
FIG. 19 is an exploded perspective view of a hand assisted laparoscopic seal assembly with another alternate attachment ring.
Figure 20:
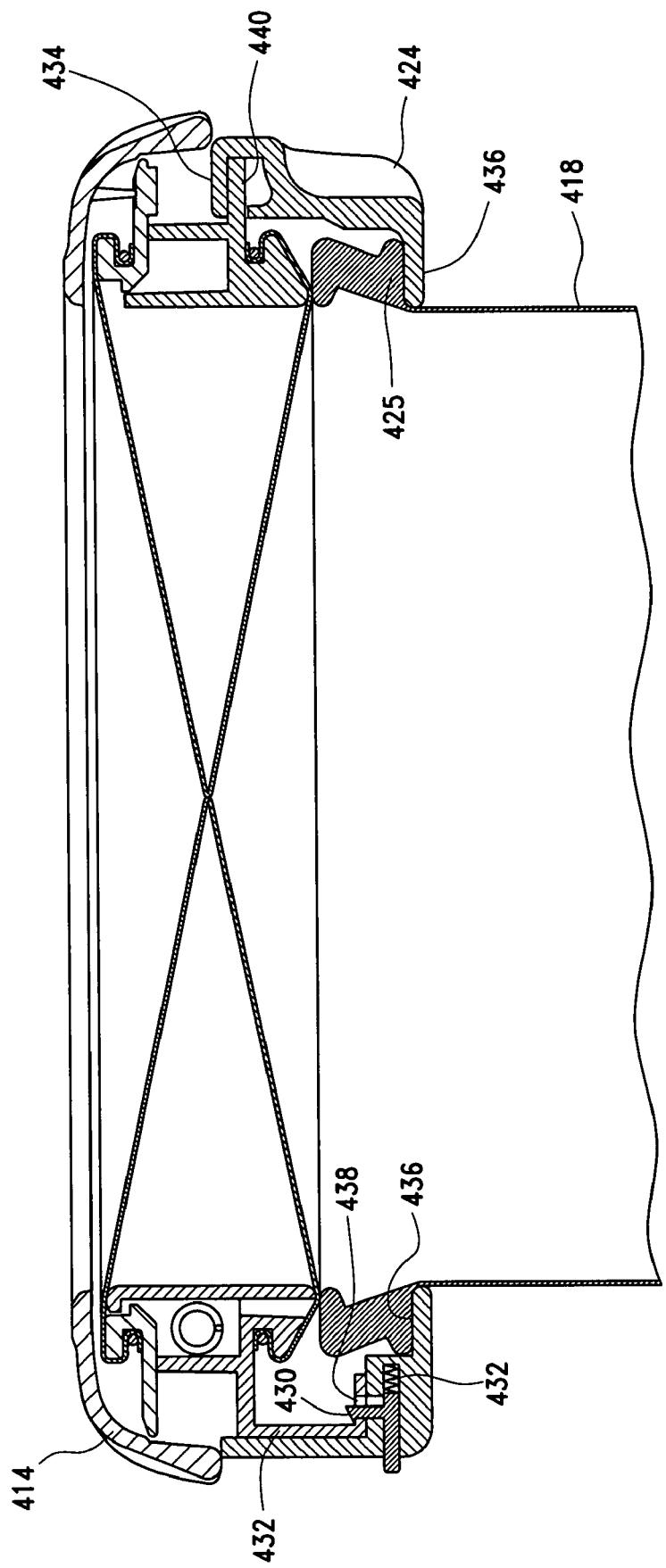
FIGS. 20 and 21 are cross sectional views showing attachment of the hand assisted laparoscopic seal assembly shown with reference to FIG. 19.
Figure 21:
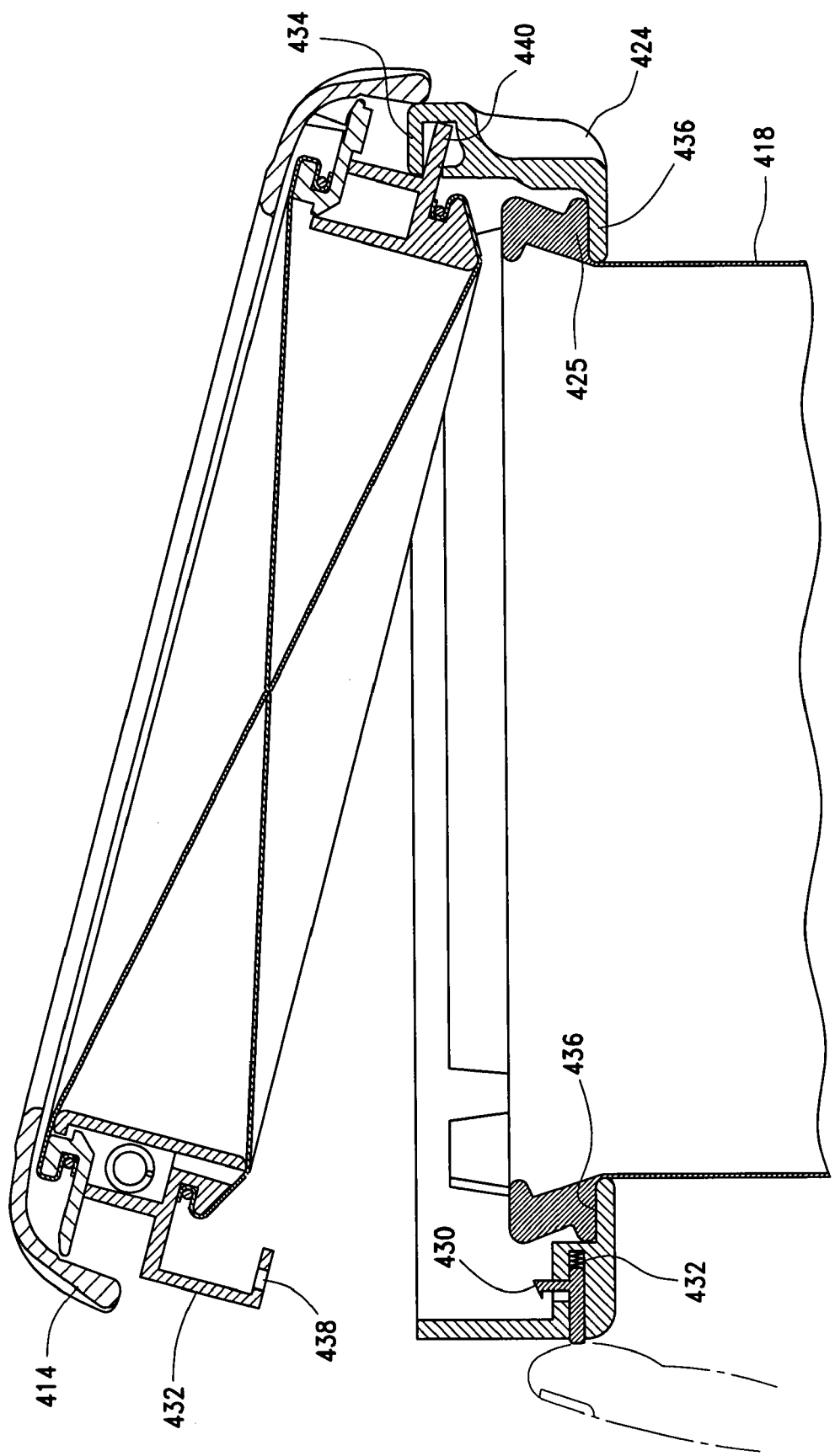

Referring to FIGS. 19, 20 and 21, yet another embodiment of an attachment ring 424 is disclosed for use in selectively securing a retractor 418 to a seal cap 414. This is achieved by providing the attachment ring 424 with an inwardly directed, first upper connecting flange 430 which is biased under the control of spring 432 for selective attachment and release of the seal cap 414 secured thereto. The attachment ring 424 is further provided with an inwardly directed, second upper connecting flange 434. The second upper connecting flange 434 is fixed and is substantially, diametrically opposed to the first upper connecting flange 430. The attachment ring 424 is further provided with an inwardly directed, lower connecting flange 436 shaped and dimensioned for receiving and supporting the upper end 425 of the retractor 418. The lower connecting flange 436 is shaped and dimensioned such that the upper end 425 of the retractor 418 is held between the bottom of the seal cap 414 and the upper surface of the lower connecting flange 436.

The first and second upper connecting flanges 430, 432 are shaped and dimensioned to seat within respective first and second recesses 438, 440 formed along the outer wall 432 of the seal cap 414. In this way, the interaction of the first and second upper connecting flanges 430, 434 with the respective first and second recesses 438, 440 results in a secure attachment of the attachment ring 424 and the seal cap 414. In practice, the upper end 425 of the retractor 418 is placed within the attachment ring 424 and positioned upon the upper surface of the lower connecting flange 436. Thereafter, the seal cap 414 is oriented at an oblique angle with respect to the attachment ring 424 such that a leading end of the seal cap 414 may be slid toward the second upper connecting flange 434 with the retractor 418 substantially positioned between the lower surface of the seal cap 414 and the upper surface of the lower connecting flange 436. At this point, the seal cap 414 is rotated, in particular, the trailing end of the seal cap 414 is rotated toward the lower connecting flange 436 such that the first upper connecting member 430 rides along the outer wall of the seal cap 414 until its seats within the recess 438, 440 formed therein. At this point, the seal cap 414 should be securely held within the attachment ring 424 with the retractor 418 held between the lower connecting flange 436 and the lower surface of the seal cap 414. The attachment ring 424, and ultimately, the seal cap 414 may be subsequently removed by simply reversing the preceding steps; generally, that is, withdrawing the first upper connecting flange 430 from the first recess 438 against the bias of the spring 432, rotating the trailing end of the seal cap 414 away from the lower connecting flange 436 and withdrawing the leading end from its position within the space defined by the attachment ring 424.

In accordance with yet a further embodiment, the attachment ring 524 is secured to the seal cap 514 via a safety cap type attachment mechanism, for example, as disclosed in U.S. Pat. No. 4,241,184, entitled "SAFETY CLOSURE ASSEMBLY WITH A SHEET METAL OVERCAP", issued Dec. 30, 1980, which is incorporated herein by reference. More particularly, and with reference to FIGS. 22, 23 and 24, the attachment ring 524 is shaped and dimensioned for selective attachment to the seal cap 514, which has a threaded neck 530. The attachment ring 524 includes an overcap 532 having a bottom wall 540 and a depending skirt 536 therearound. The skirt 536 has a radially inwardly directed retaining rim 534 holding the inner cap 550 within the overcap 532. The bottom wall 540 of the overcap 532 has a plurality of louvers 538 arranged in a circular configuration. Each louver 538 includes a flange portion 546 which projects downwardly at an angle from the bottom wall 540, and which terminates in a terminal edge 542 in the bottom wall 540.

Figure 22:
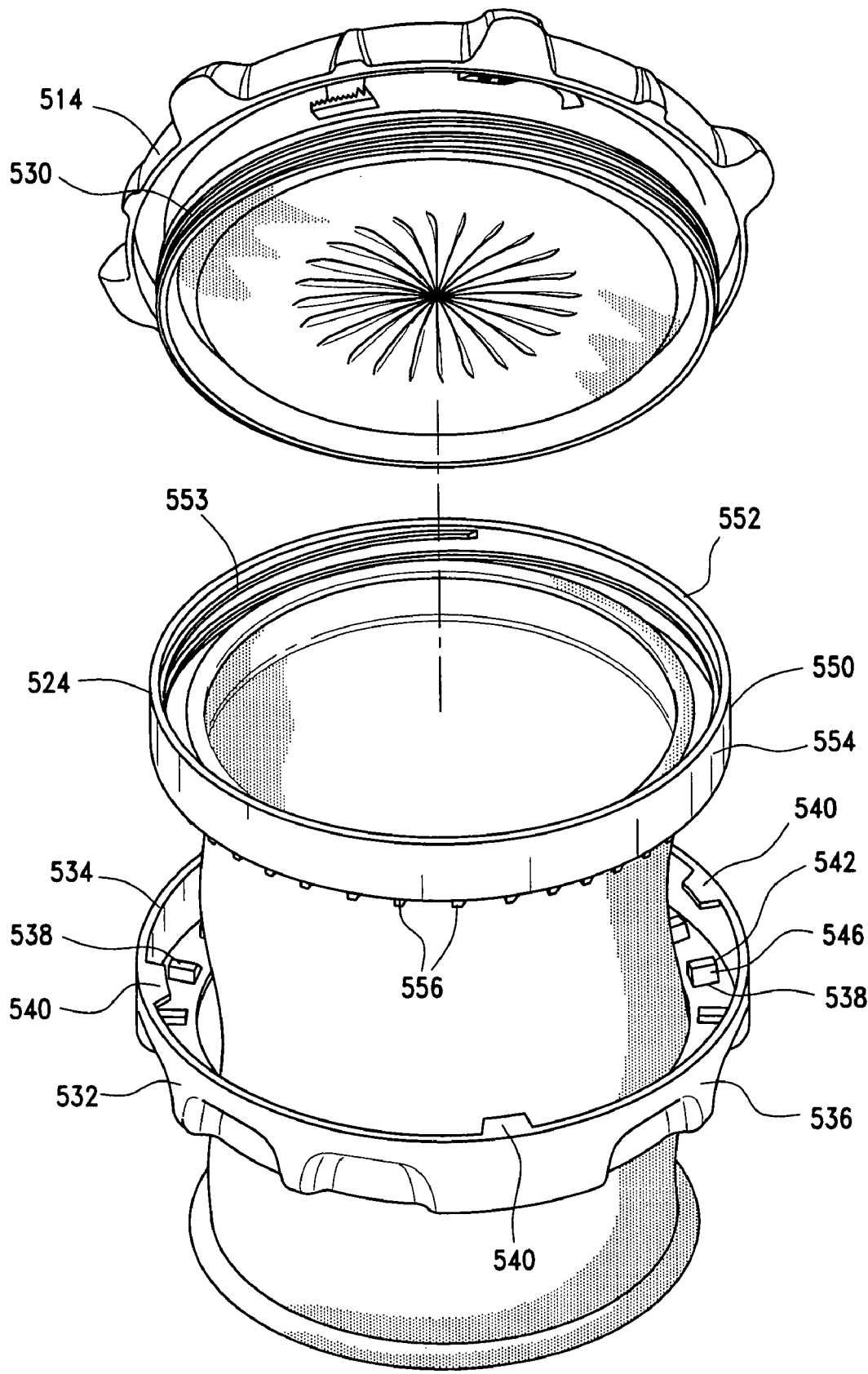
FIG. 22 is an exploded perspective view of a hand assisted laparoscopic seal assembly with yet another alternate attachment ring.
Figure 23:
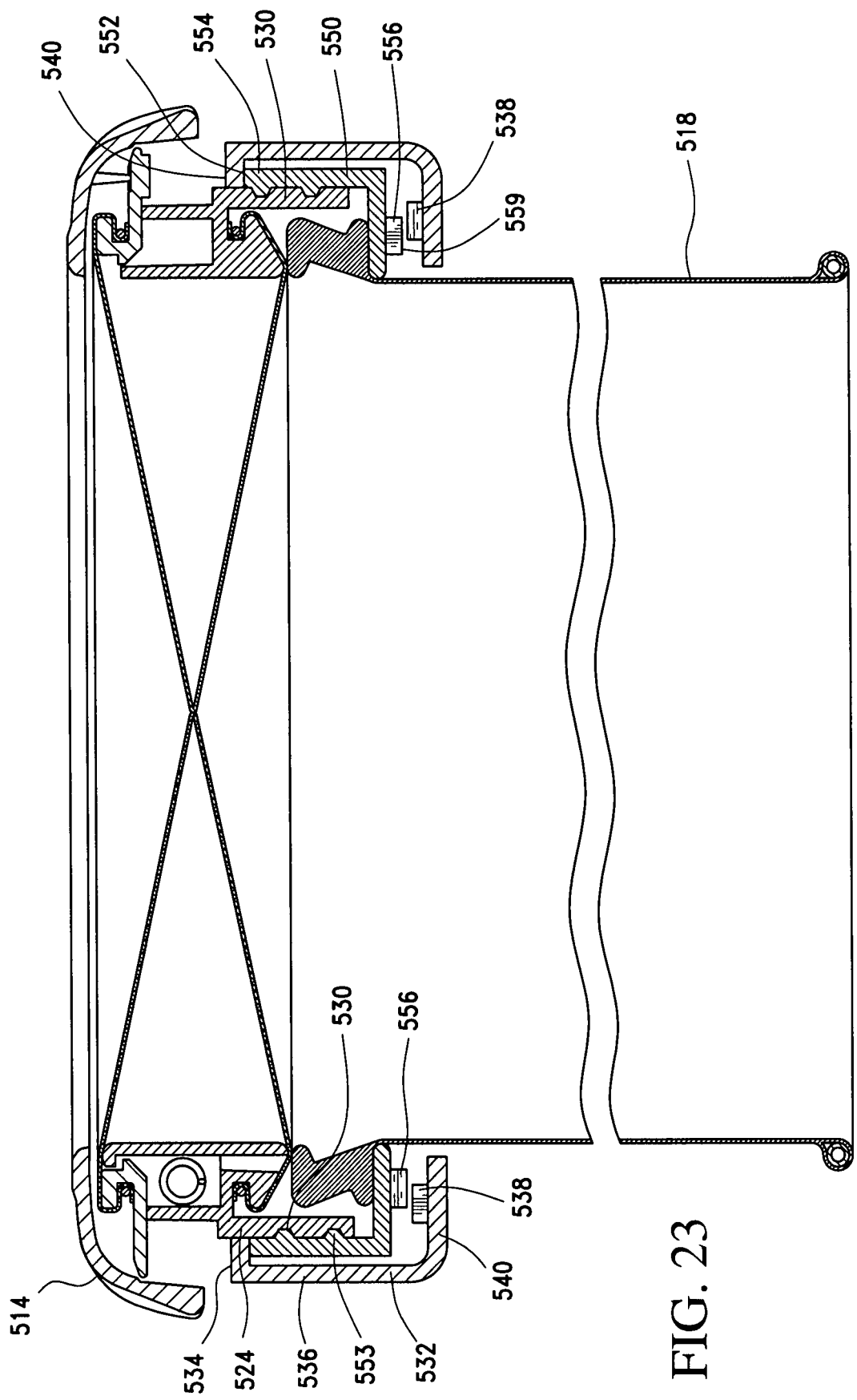
FIGS. 23 and 24 are cross sectional views showing operation of the hand assisted laparoscopic seal assembly shown with reference to FIG. 22.
Figure 24:
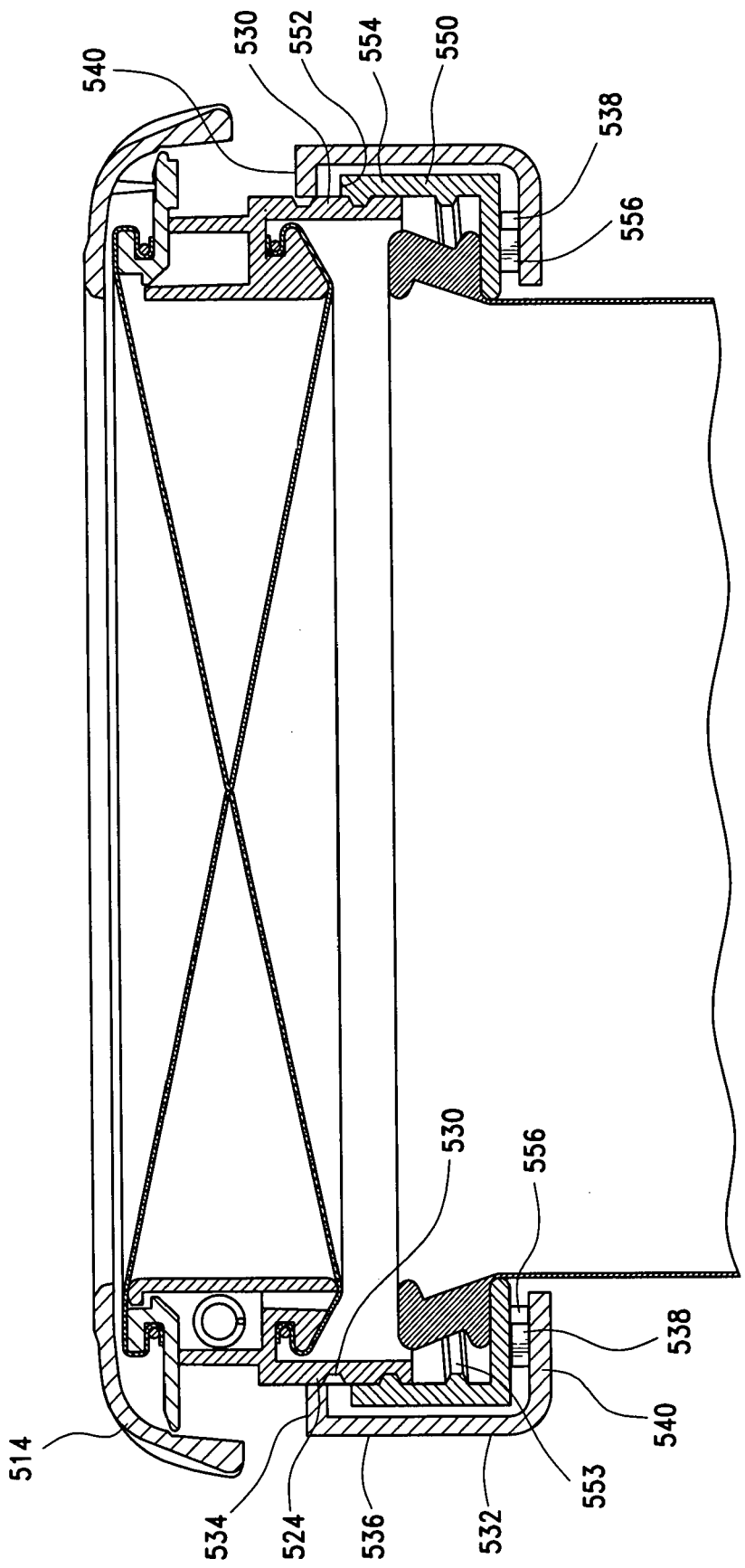

FIGS. 22, 23 and 24 illustrate the inner cap 550 of the attachment ring 524. The cap 550 includes a top edge 552 with a downwardly depending skirt 554 therearound. In addition, the cap 550 includes internal threads 553 for cooperatively engaging against the threaded neck 530 of the seal cap 514. The bottom wall 551 of the inner cap 550 further includes a plurality of teeth 556, preferably arranged in a circular configuration. The inner cap 550 is adapted to be disposed within the overcap 532 and retained therein by the bottom wall 540, the retaining rim 534 and the skirt 536. The skirt 554 of the inner cap 550 is somewhat shorter than the skirt 536 of the overcap 532, so that limited axial displacement is possible between the inner cap 550 and the overcap 532. The louvers 538 of the overcap 532 are adapted for cooperative engagement with the teeth 556 of the inner cap 550. However, because of the loose mounting of the inner cap 550 within the overcap 532, the overcap 532 may be rotated freely with respect to the inner cap 550 when the closure members are axially displaced from each other.

FIG. 24 illustrates the cooperative engagement between the louvers 538 of the overcap 532 with the teeth 556 of the inner cap 550 when a minimal force is applied upwardly to the overcap 532 while turning it in either the attachment ring-applying direction or the attachment ring-removing direction. When appropriate force is applied and the overcap 532 turned in either the applying or the removing direction, the teeth 556 engage the louver 538 for attachment or removal of the attachment ring 524.

Figure 25:
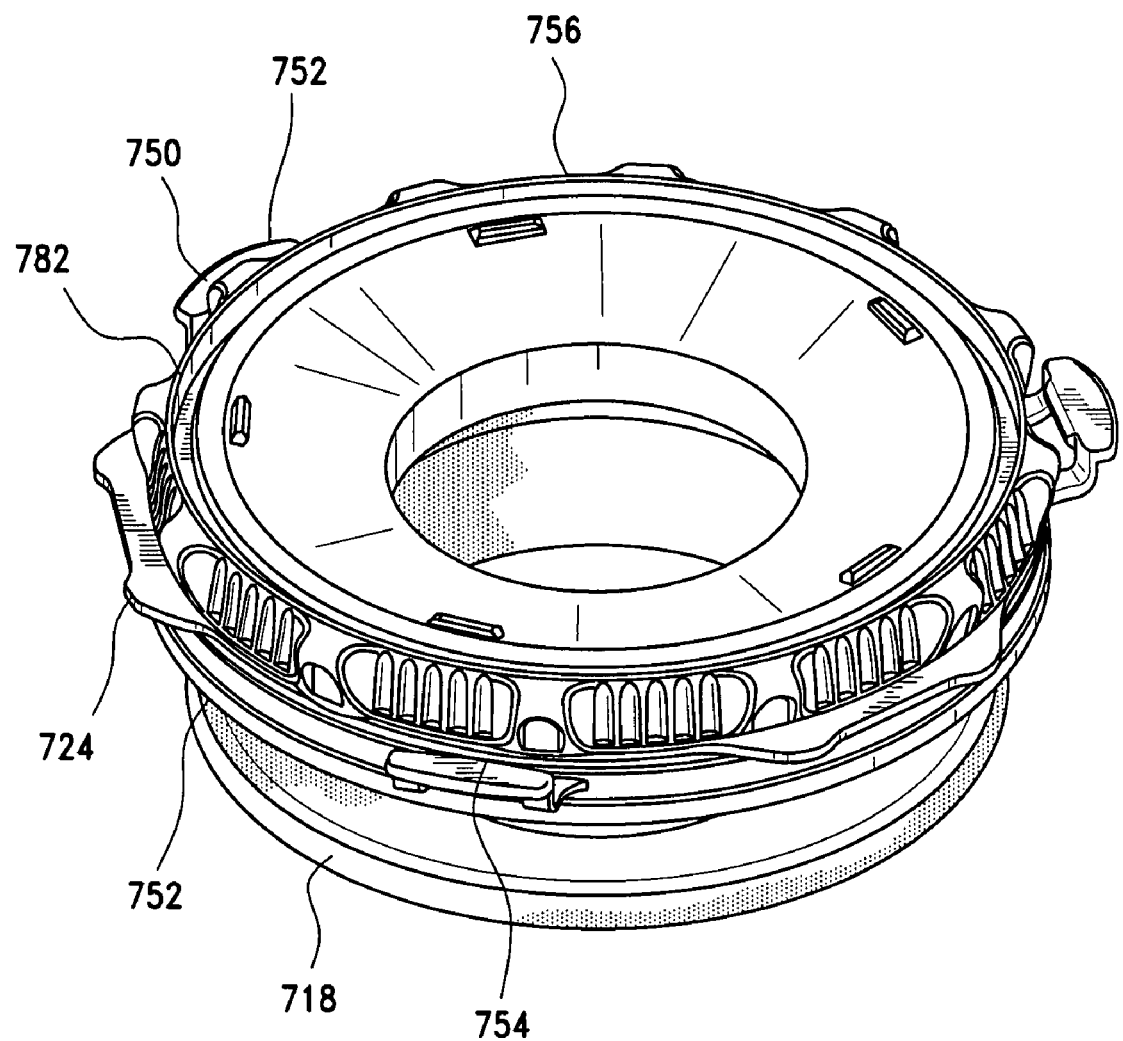
FIGS. 25, 26 and 27 are various views of a hand assisted laparoscopic seal assembly with yet another embodiment of an attachment ring.
Figure 26:
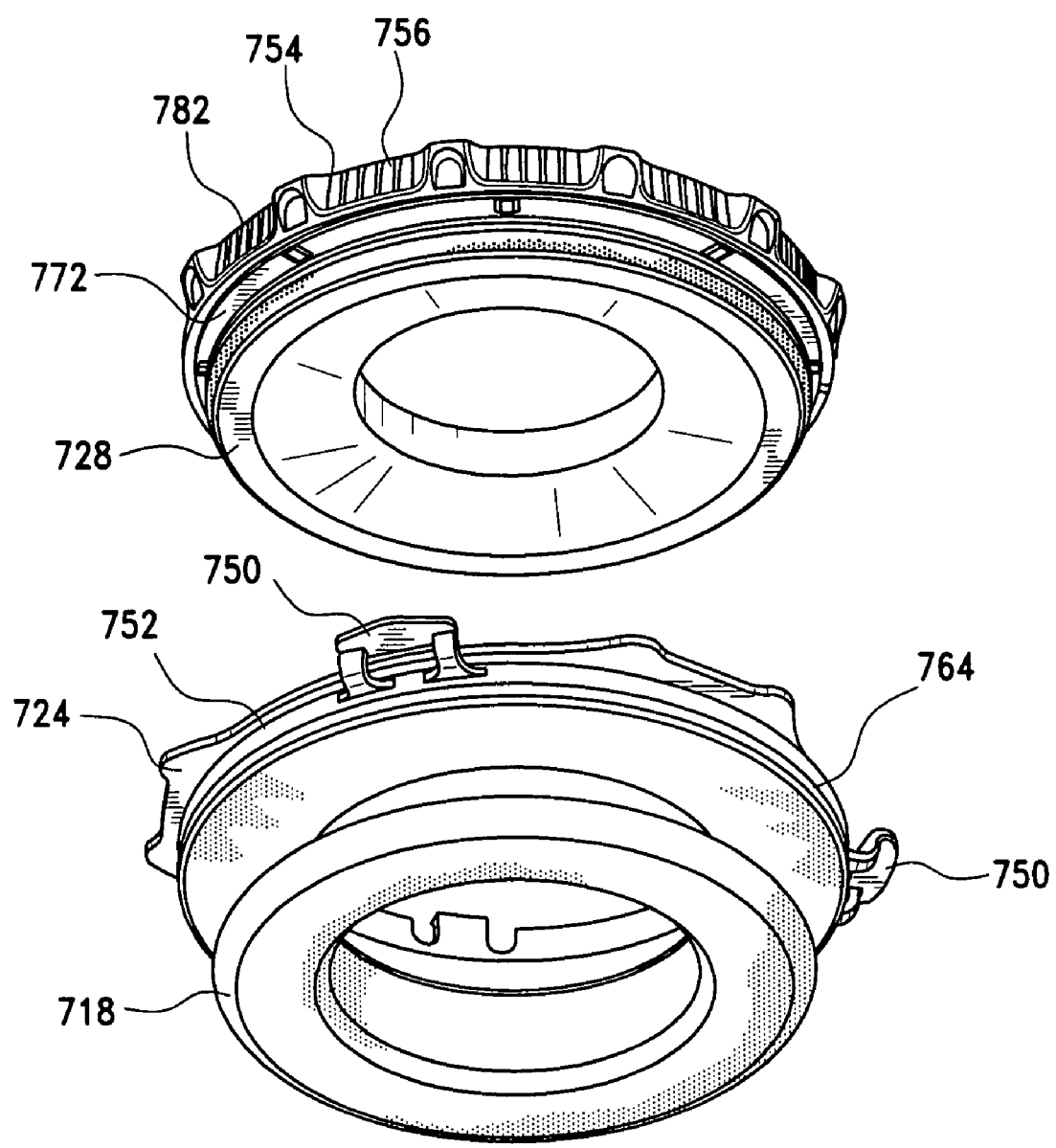
Figure 27:
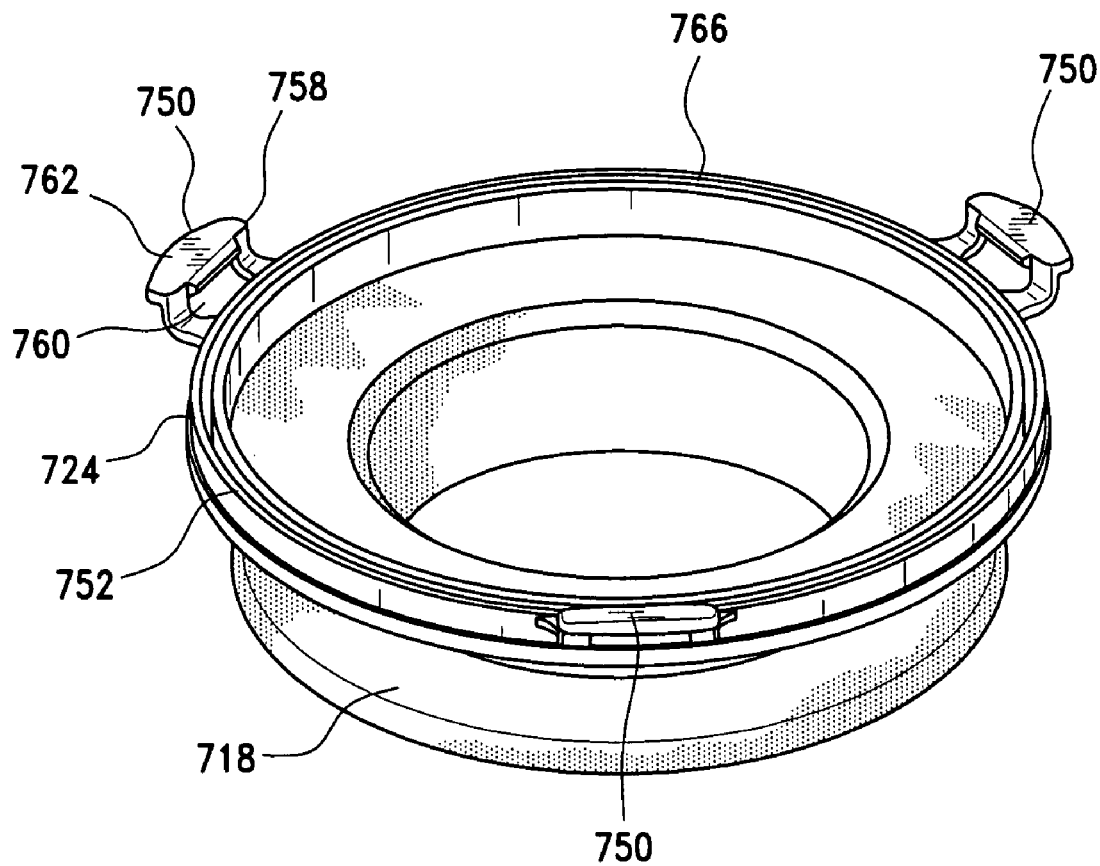

In accordance with yet a further embodiment, and with reference to FIGS. 25, 26 and 27, selective attachment and detachment of the attachment ring 724 to the lower seal ring 728 is achieved through the provision of resiliently biased latches 750 along an outer surface 752 of the attachment ring 724. The latches 750 are shaped and dimensioned to engage an outwardly extending lip 754 along the outer surface 756 of the ergonomic cover member 782, which is secured to the upper seal ring 772, in a manner securely holding the attachment ring 724 in position adjacent the lower seal ring 728.

More particularly, the attachment ring 724 is provided with a plurality of outwardly and upwardly extending resiliently biased latches 750, in accordance with a preferred embodiment, three such latches. Each latch 750 includes a latch body 758 having a central aperture 760 formed therein. The central aperture 760 is shaped and dimensioned for receiving respective outwardly extending lip 754 formed along the outer surface 756 of the ergonomic cover member 782. As such, the central aperture 760 is defined by an obliquely angled wall 762 which engages the outwardly extending lip 754 in manner substantially preventing inadvertent disconnection of the latch 750 from the outwardly extending lip 754. As with the prior embodiments, this attachment ring 724 also includes an inwardly directed ledge 764 upon which the upper end 766 of the retractor 718 is supported.

With this in mind, the attachment ring 724 is coupled to the upper and lower seal rings 772, 728 by bringing the attachment ring 724 toward the lower seal ring 728, aligning the latches 750 with the outwardly extending lip 754 and bringing the latches 750 into engagement with the outwardly extending lip 754. When it is desired to remove the attachment ring 724, one need only bias the latches 750 outwardly such that the outwardly extending lip 754 is removed from the central aperture 760 and move the attachment ring 724 away from the lower seal ring 728.

With regard to the upper end of the retractor, it is preferably as disclosed in commonly owned U.S. patent application Ser. Nos. 11/458,325, filed Jul. 18, 2006, entitled "ROLL-UP WOUND PROTECTOR WITH TRICUSPIDATE RING", 11/458,328, filed Jul. 18, 2006, entitled "ROLL-UP WOUND PROTECTOR WITH ASYMMETRIC RING", and 11/458,329, filed Jul. 18, 2006, entitled "ROLL-UP WOUND PROTECTOR", which are incorporated herein by reference.

In accordance with a preferred embodiment, the iris seal 12 is a rotatable seal which selectively opens to permit passage of a surgeon's hand therethrough and automatically closes in a manner creating a gas tight barrier between the interior abdominal space and the external environment whether or not a hand or instrument 68 is inserted through the seal assembly 10. In particular, the housing 16 in which the iris seal 12 is supported includes a lower seal ring 28 having a track 70 which supports an upper seal ring 72 for relative rotational motion in a manner discussed below in greater detail.

As will be discussed below in greater detail, the upper end 74 of the iris seal 12 is permanently connected to the upper seal ring 72. The lower end 76 of the iris seal 12 is permanently connected to the lower seal ring 28. The upper seal ring 72 and the lower seal ring 28 are connected together for relative rotational movement in a manner allowing for opening and closing of the iris seal 12. In accordance with a preferred embodiment, the upper seal ring 72 and the lower seal ring 28 are connected by at least three snap tabs 78 located on the lower seal ring 28 that are shaped and dimensioned to engage a recess 80 along the inner edge of the upper seal ring 72.

An ergonomic cover member 82 is secured to the upper seal ring 72. The ergonomic cover member 82 includes a contoured outer surface 84 providing for improved handling and twisting of the upper seal ring 72 for opening and closing the iris seal 12 in accordance with the present invention. In accordance with a preferred embodiment, the ergonomic cover member 82 is a separate component fixedly secured to upper seal ring 72 such that rotational force applied to the ergonomic cover member 82 is transmitted on to the upper seal ring 72 for opening and closing of the iris seal 12. However, and as those skilled in the art will certainly appreciate, the ergonomic cover member 82 could be integrally formed with the upper seal ring 72, while still remaining within the spirit of the present invention.

Referring to FIGS. 4, 5, 6, 7 and 8, as discussed below in greater detail, the iris seal 12 is secured between the upper seal ring 72 and the lower seal ring 28. The upper seal ring 72 is supported within a track 70 of the lower seal ring 28 in a manner facilitating rotational movement between the upper seal ring 72 and the lower seal ring 28. In this way, the rotational movement of the upper seal ring 72 relative to the lower seal ring 28 is utilized to control the opening and closing of the iris seal 12 for one-hand insertion of a hand through the present seal assembly 10.

The iris seal 12 is mounted between the upper seal ring 72 and the lower seal ring 28 such that upon rotation of the upper seal ring 72 in a predetermined direction, the central access opening 86 of the iris seal 12 will open, providing a surgeon with an access opening 86 for passage of his hand therethrough. Automatically the upper seal ring 72, and ultimately, the iris seal 12 will rotate in the reverse direction, the access opening 86 will close securely about the wrist of the surgeon or instrument. That is, the upper seal ring 72 and the iris seal 12 are moved between open orientations (see FIGS. 5, 6 and 8) in which an access opening 86 is created within the iris seal 12 and a closed orientation (see FIGS. 4 and 7) in which the iris seal 12 is either wrapped about the wrist of a user with his or her hand inserted therein or substantially fully closed when the iris seal 12 is not in use.

Opening and closing of the iris seal 12 is achieved by constructing the iris seal 12 in a folded configuration spanning the upper seal ring 72 and the lower seal ring 28 in a substantially taut configuration. As such, rotation of the upper seal ring 72 in a first direction will result in an increase of tension along the iris seal 12 in a manner drawing the fold outwardly opening the central access opening 86 in the iris seal 12.

Figure 8:
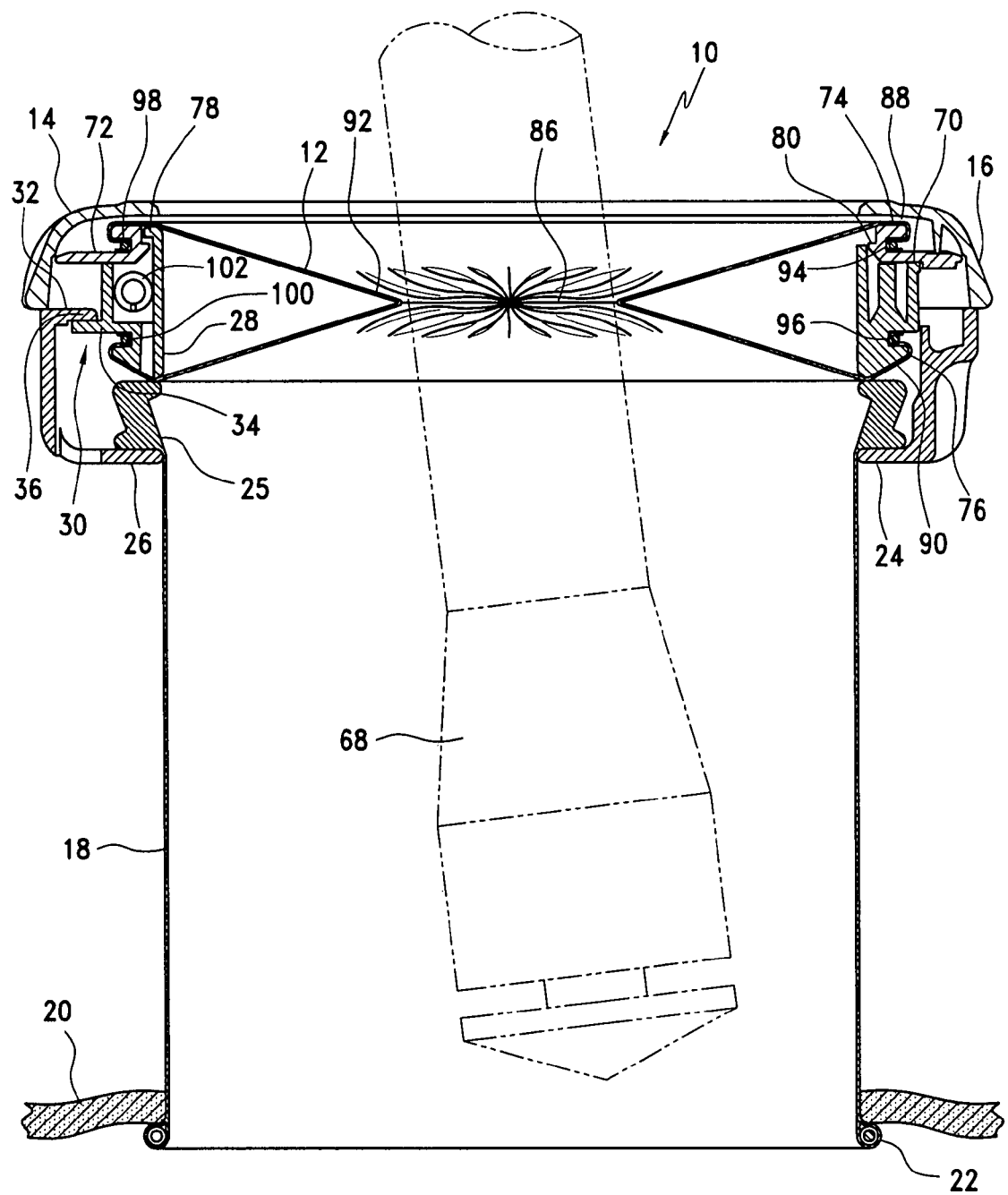
FIG. 8 is a cross sectional view taken along the line 8-8 in FIG. 6 with an instrument shown in phantom.

In accordance with the preferred embodiment, the iris seal 12 is composed of a rubber like member. The rubber like member is constructed in the shape of a cylindrical section with the upper and lower sections 88, 90 thereof having a wider diameter than the central section 92 (thereby offering a cross-section as shown in FIGS. 7 and 8). As will be appreciated based upon the following disclosure, the construction of the rubber like member creates a substantially planar iris seal 12 which is closed or opened when the upper seal ring 72 and the lower seal ring 28 are relatively rotated in opposite directions.

In accordance with a preferred embodiment, the rubber like member is formed from a thin film having a thickness of less than approximately 0.025" and made from a material having elasticity, such as, natural rubber, synthetic rubber, poly vinyl chloride, silicon and a variety of elastomers (for example, urethane, polyisoprene, silicone). As briefly mentioned above, the rubber like member is cylindrical and includes a central access opening 86 having a predetermined cross sectional area at the central section 92 thereof. The rubber like member is shaped such that the diameter of the opening decreases in the direction from the upper and lower sections to the central section 92 of the rubber like member. Furthermore, the upper and lower ends 74, 76 of the iris seal 12, which are fitted into the grooves 94, 96 of the upper seal ring 72 and the lower seal ring 28 and held therein with O-rings 98, 100, allow for detachment from the upper seal ring 72 and the lower seal ring 28. In accordance with a preferred embodiment, the O-rings are integrated into the iris seal, minimizing components and material cost. Because of such detachable structure of the rubber like member, it can be easily replaced by a fresh member when the used rubber like member is broken or worn. This technique would be useful for reusable devices.

Figure 5:
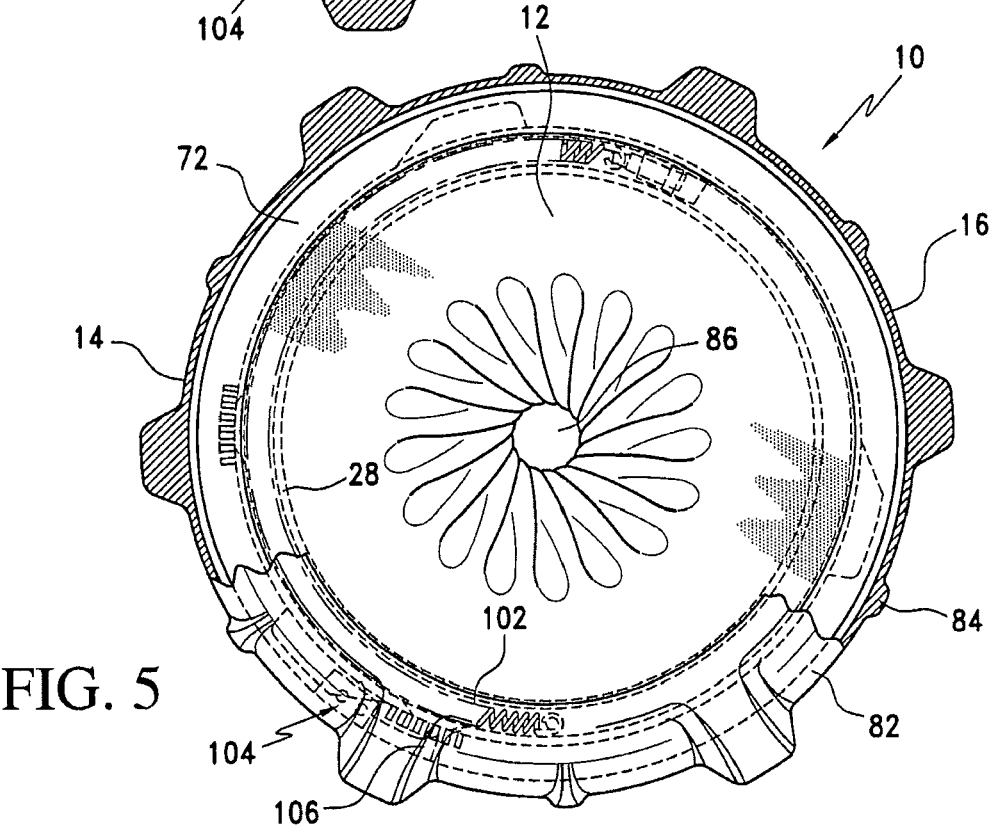

Referring to FIGS. 4, 5, 6, 7 and 8, a plan view and a sectional view are presented, showing the iris seal 12 in its respective closed and open states. FIGS. 6 and 8 show the iris seal 12 in a fully opened orientation for viewing within the cavity or insertion of an instrument or hand therethrough, while FIG. 5 shows a partially opened orientation sufficient for passing a hand therethrough when sealing thereabout is desired.

This open state is created when the upper seal ring 72 is rotated at a predetermined angle, for example, 15 degrees, from the closed state of the iris seal 12, and the access opening 86 is created.

Figure 12:
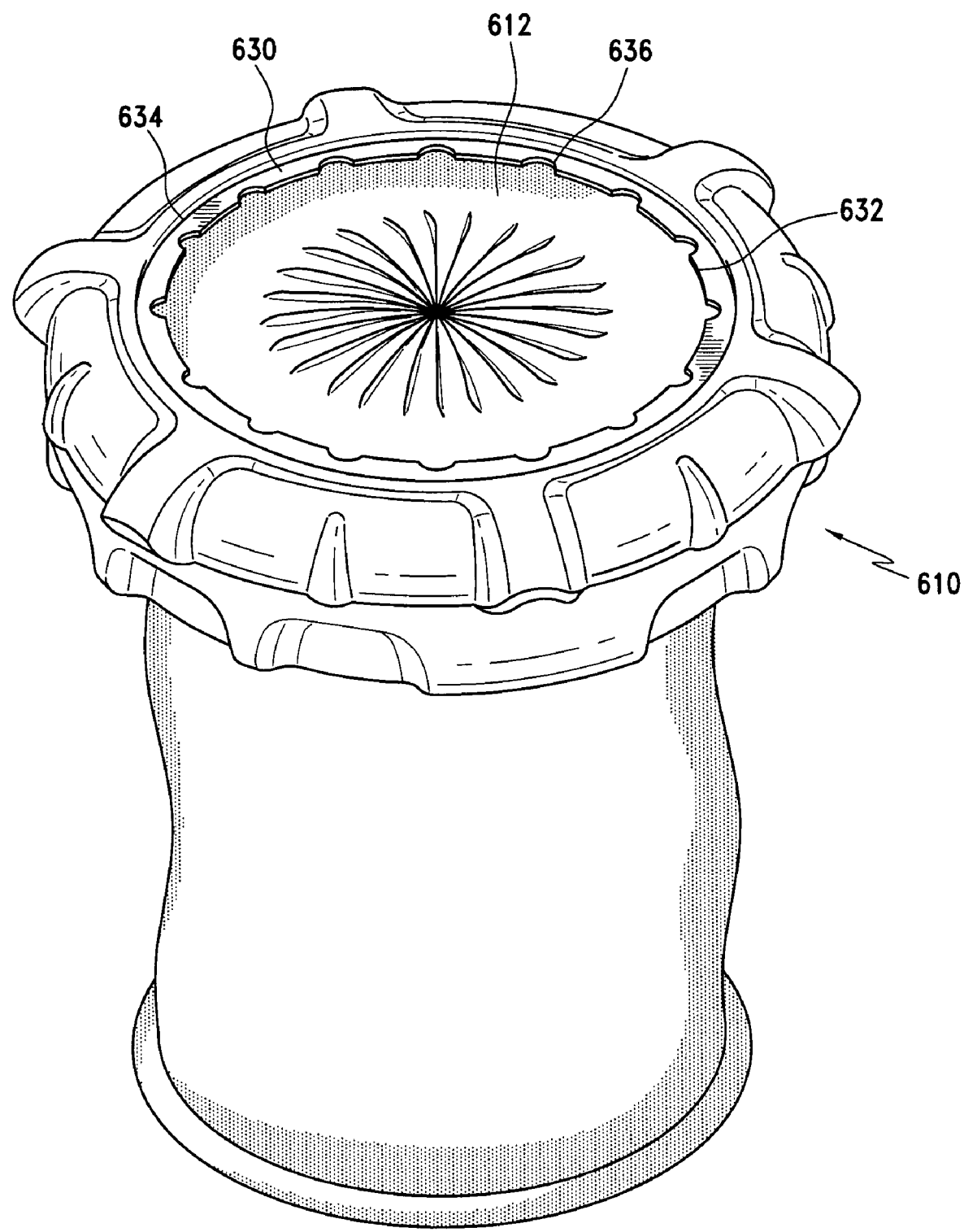
FIG. 12 is a perspective view of a hand assisted laparoscopic seal assembly in accordance with an alternate embodiment.

In accordance with an alternate embodiment, and with reference to FIG. 12, improved access to the movement of the upper seal ring, and ultimately, the iris seal 612, is achieved by the provision of a contoured ring 630 secured to the upper surface of the upper seal ring. The contoured ring 630 is substantially annular and includes an inner circumference 632 and an outer circumference 634. The outer circumference 634 is substantially smooth and conforms to the profile of the upper seal ring. However, the inner circumference 632 is formed with a series of recesses 636 shaped and dimensioned for receiving the fingers of a medical practitioner attempting to use the present seal assembly 610. In particular, the recesses 363 are shaped and dimensioned such that an individual wishing to use the present seal assembly 610 may seat his or her fingers therein and rotate the contoured ring, and the upper seal ring to which the contoured ring 630 is rigidly attached, and ultimately the iris seal 612 with only one hand. While the iris seal 612 is in its open orientation, the user may simply slip his or her hand through the iris seal 612 and proceed with the surgical procedure with minimal loss of insufflation. This feature allows the physician's other hand to be free and undisrupted, allowing the surgeon to maintain his procedural focus and position with the free hand during hand exchanges.

In accordance with a preferred embodiment, the upper seal ring 72 is biased relative to the lower seal ring 28 by a spring 102 to immediately return to the closed orientation upon rotation of the upper seal ring 72 relative to the lower seal ring 28 to its open orientation with subsequent release thereof. As such, the surgeon may rotate the upper seal ring 72 relative to the lower seal ring 28 through engagement of the contoured surface of the ergonomic cover member 82, the contoured ring 530 (in accordance with the embodiment shown with reference to FIG. 12) or, by direct engagement with the iris seal 12 to move the iris seal 12 from its closed orientation to an open orientation opening the access opening 86 for passage of his or her hand therethrough. Once his or her hand is passed therethrough, the upper seal ring 72, ergonomic cover member 82, contoured ring 530 and/or the iris seal 12 are released allowing the action of the spring 102 to move the upper seal ring 72 and the iris seal 12 back toward the closed orientation.

As some surgeons may want to maintain an open position using the autoclosing device, a ratchet mechanism 104 has been developed wherein the surgeon has control over the spring biased action moving the upper seal ring 72 relative to the lower seal ring 28 and iris seal 12 from its open orientation to its closed orientation. Although a ratchet system is disclosed in accordance with a preferred embodiment of the present invention, those skilled in the art will appreciate that a seal assembly without a ratchet assembly could also be practiced within the spirit of the present invention.

In accordance with a preferred embodiment, and with reference to FIGS. 3 to 11, the upper seal ring 72 is seated within the track 70 of the lower seal ring 28 with the spring 102 biasing the upper seal ring 72 relative to the lower seal ring 28 for movement relative thereto opening the access opening 86. However, a ratchet mechanism 104 is positioned between the upper seal ring 72 and the lower seal ring 28. The ratchet mechanism 104 includes a ratchet arm 106 secured to the upper seal ring 72 which is oriented to engage upwardly facing first and second ratchet surfaces 108*a*, 108*b* composed of a plurality of ratchet teeth 109*a*, 109*b* on the lower seal ring 28 which functions to hold the upper seal ring 72 relative to the lower seal ring 28 as it is moved to an open orientation. In practice, the ratchet arm 106 is shaped and dimensioned to engage the teeth 109*a*, 109*b* of the ratchet surfaces 108*a*, 108*b* when rotated in a first direction (for example, and in accordance with a preferred embodiment, clockwise rotation when viewed from above). However, once the upper seal ring 72 is rotated such that the ratchet arm 106 moves beyond the rear ends 110*a*, 110*b* of the ratchet surfaces 108*a*, 108*b*, the ratchet arm 106 is free to move past the ratchet surfaces 108*a*, 108*b* as the upper surface ring 72 is rotated in a second direction opposite the first direction.

This is achieved by providing the ratchet arm 106 with a tapered distal end 112 which is biased by similar tapered surfaces 114*a*, 114*b* on the respective rear ends 110*a*, 110*b* of the ratchet surfaces 108*a*, 108*b* to ride under the ratchet surfaces 108*a*, 108*b* as the upper seal ring 72 is rotated relative to the lower seal ring 28 in a second direction. However, when the upper seal ring 72 is rotated in a first direction, the distal end 112 of the ratchet arm 106 is biased to ride over the upper surface of the ratchet surfaces 108*a*, 108*b* such that it engages the various teeth 109*a*, 109*b* to control movement of the upper seal ring 72 relative to the lower seal ring 28.

In accordance with a preferred embodiment of the present invention, first and second ratchet surfaces 108*a*, 108*b* are provided. The first ratchet surface 108*a* engages the ratchet arm 106 when the upper and lower seal rings 72, 28 are oriented to provide a relatively small opening in the iris seal 12 through which a medical practitioner may pass his or her hand to gain access to a body cavity. The configuration is especially suited to single hand interactions where a user may rotate the upper seal ring 72 relative to the lower seal ring 28 with the same hand which is to be passed through the present seal assembly 10. In particular, and as a result of the ratchet mechanism 104, a user may, for example, use his or her left hand to rotate the upper seal ring 72 relative to the lower seal ring 28 in a manner slightly or partially opening the iris seal 12 as shown in FIG. 5. When in this position, the audible click sound and slight resistance produced as the ratchet arm 106 moves over the first ratchet surface 108*a* will provide the user with an indication a stopping position has been reached. At this point, the user may release the upper seal ring 72 without fear that the iris seal 12 will snap back to its closed orientation. Rather the ratchet mechanism 104 holds the upper and lower seal rings 72, 28 relative to each other, allowing the user to slip his or her hand through the opening in the iris seal 12. As the user pushes his or her hand through the iris seal 12, the outward force causes a slight rotation of the upper seal ring 72 relative to the lower seal ring 28 in a manner disengaging the ratchet arm 106 from the first ratchet surface 108*a*, and allowing the upper seal ring 72 to rotate relative to the lower seal ring 28 under the bias of the spring 102 to move the iris seal 12 back to its closed orientation, securely wrapping it about the user's wrist/forearm. As such, when the user pulls his or her arm from the seal assembly 10, the iris seal 12 will automatically close sealing the body cavity from the external environment.

The second ratchet surface 108b allows the seal assembly 10 to be locked with the central access opening 86 in a larger open configuration allowing for more complete access to the body cavity. As those skilled in the art will certainly appreciate, it is at times desirable to provide a large access opening to the body cavity. As such, the present seal assembly 10 is provided with a second ratchet surface 108b providing for locking of the upper seal ring 72 and the lower seal ring 28 relative to each other when the iris seal 12 is more fully opened as shown in FIG. 6.

As with the first ratchet surface 108a, the second ratchet surface 78b engages the ratchet arm 76 when the upper and lower seal rings 72, 28 are oriented in a particular orientation providing, in this case, a relatively large opening in the iris seal 12. A user rotates the upper seal ring 72 relative to the lower seal ring 28 to create an opening in the iris seal 12 beyond the small opening as shown in FIG. 5. Once the first ratchet surface 108a is passed (as indicated by the first series of audible clicks), the audible clicking sound produced as the ratchet arm 106 moves over the second ratchet surface 108b will provide the user with an indication a stopping position has been reached. At this point, the user may release the upper seal ring 72 without fear that the iris seal 12 will close, and proceed to utilize the large opening for access to the body cavity in a desired manner. When the user no longer requires this access, he or she may simply rotate the upper seal ring 72 relative to the lower seal ring 28 in a first direction slightly opening the iris seal 12, at which point the ratchet arm 106 will disengage from the second ratchet surface 108b and allow the upper seal ring 72 to rotate relative to the lower seal ring 28 under the bias of the spring 102 to move the iris seal 12 back to its closed orientation.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A seal assembly for permitting hand assisted laparoscopic procedures, comprising:

a seal cap having a central access opening allowing access to a body cavity as desired, the seal cap is provided with a housing in which a seal is positioned;

the seal cap also includes an attachment ring that is selectively detachable and attachable to the seal cap for selective attachment of a retractor, wherein the seal cap includes a recess formed along an outer circumference of the seal cap and the attachment ring includes an inwardly directed flange shaped and dimensioned to seat within the recess of the seal cap; and wherein the attachment ring includes an inwardly directed ledge upon which an upper end of the retractor is seated to securely position it between the attachment ring and a lower member of the housing; and wherein the attachment ring is constructed with a first semi-circular member and a second semi-circular member, the first semi-circular member and the second semi-circular members are respectively provided with a first latch member and a mating second latch member shaped and dimensioned to provide for selective coupling and decoupling of the first semi-circular member and the second semi-circular member.

2. The seal assembly according to claim 1, wherein the seal cap includes an iris seal positioned within the housing.

3. The seal assembly according to claim 1, wherein the seal cap includes an upper seal ring and a lower seal ring, and the attachment ring is selectively secured to the lower seal ring.

4. The seal assembly according to claim 3, wherein each of the first semi-circular member and the second semi-circular member includes a first end and second end, the respective first ends of the first semi-circular member and the second semi-circular members are connected via a living hinge in a manner allowing the first semi-circular member and the second semi-circular member to pivot relative to each other, and the second ends of the first semi-circular member and the second semi-circular members are respectively provided with the first latch member and the mating second mating latch member shaped and dimensioned to provide for selective coupling and decoupling of the second ends of the first semi-circular member and the second semi-circular member.

* * * * *